(12) United States Patent
Hartikka et al.

(10) Patent No.: US 9,102,950 B2
(45) Date of Patent: Aug. 11, 2015

(54) COMPOSITIONS AND METHODS FOR ENHANCING IMMUNE RESPONSES TO VACCINES

(71) Applicant: Vical Incorporated, San Diego, CA (US)

(72) Inventors: Jukka Hartikka, La Mesa, AZ (US); Sean M. Sullivan, San Diego, CA (US); Joel D. Enas, Fallbrook, CA (US); Alain P. Rolland, San Diego, CA (US)

(73) Assignee: Vical Incorporated, San Diego, CA (US)

( * ) Notice: Subject to any disclaimer, the term of this patent is extended or adjusted under 35 U.S.C. 154(b) by 0 days.

(21) Appl. No.: 13/835,806

(22) Filed: Mar. 15, 2013

(65) Prior Publication Data

US 2013/0202630 A1 Aug. 8, 2013

Related U.S. Application Data

(60) Continuation of application No. 13/566,892, filed on Aug. 3, 2012, now Pat. No. 8,999,345, which is a division of application No. 13/243,692, filed on Sep. 23, 2011, now abandoned, which is a division of application No. 12/126,787, filed on May 23, 2008, now abandoned.

(60) Provisional application No. 60/939,702, filed on May 23, 2007, provisional application No. 61/044,338, filed on Apr. 11, 2008.

(51) Int. Cl.
*A61K 39/39* (2006.01)
*A61P 37/04* (2006.01)
*A61K 39/00* (2006.01)
*C12N 15/88* (2006.01)
*C07C 217/28* (2006.01)
*C07D 211/44* (2006.01)

(52) U.S. Cl.
CPC ............... *C12N 15/88* (2013.01); *A61K 39/39* (2013.01); *C07C 217/28* (2013.01); *C07D 211/44* (2013.01)

(58) Field of Classification Search
CPC ..... A61K 39/39; C07D 211/44; C07C 217/28
USPC ............ 424/184.1, 283.1, 450; 435/375, 440, 435/455, 458; 514/44
See application file for complete search history.

(56) References Cited

U.S. PATENT DOCUMENTS

| | | | |
|---|---|---|---|
| 5,264,618 A | 11/1993 | Felgner | |
| 5,383,851 A | 1/1995 | McKinnon | |
| 5,399,163 A | 3/1995 | Peterson | |
| 5,580,859 A | 12/1996 | Felgner | |
| 5,589,466 A | 12/1996 | Felgner | |
| 5,676,954 A | 10/1997 | Brigham | |
| 5,693,622 A | 12/1997 | Wolff | |
| 5,703,055 A | 12/1997 | Felgner | |
| 6,586,405 B2 | 7/2003 | Semple | |
| 6,670,332 B1 | 12/2003 | Wheeler | |
| 6,752,780 B2 | 6/2004 | Stout | |
| 7,105,574 B1 | 9/2006 | Wheeler | |
| 2005/0245446 A1* | 11/2005 | Hailes et al. | ................. 514/12 |
| 2008/0213306 A1* | 9/2008 | Wheeler | ................. 424/204.1 |

FOREIGN PATENT DOCUMENTS

| | | |
|---|---|---|
| WO | WO94/05624 A1 | 3/1994 |
| WO | WO94/15624 A1 | 7/1994 |
| WO | WO94/29469 A1 | 12/1994 |
| WO | WO98/14439 A2 | 4/1998 |
| WO | WO 2004060363 A1 * | 7/2004 |
| WO | WO2004/105697 A2 | 12/2004 |

OTHER PUBLICATIONS

Felgner PL., et al. "Lipofection: a highly efficient, lipid-mediated DNA-transfection procedure." Proc Natl Acad Sci U S A. Nov. 1987; 84(21):7413-7.

Felgner PL., et al. "Gene therapeutics." Nature. Jan. 24, 1991; 349(6307):351-2.

Felgner PL. "Nonviral strategies for gene therapy." Sci Am. Jun. 1997; 276(6):102-6.

Ferrari ME., et al. "Synergy between cationic lipid and co-lipid determines the macroscopic structure and transfection activity of lipoplexes." Nucleic Acids Res. Apr. 15, 2002; 30(8):1808-16.

Gramzinski RA., et al. "Immune response to a hepatitis B DNA vaccine in Aotus monkeys: a comparison of vaccine formulation, route, and method of administration." Mol Med. Feb. 1998; 4(2):109-18.

Gregoriadis G., et al. "Liposome-mediated DNA vaccination." FEBS Lett. Feb. 3, 1997;402(2-3):107-10.

Hartikka J., et al. "Physical characterization and in vivo evaluation of poloxamer-based DNA vaccine formulations." J Gene Med. Jul. 2008; 10(7):770-82.

Hartikka J., et al. "Vaxfectin enhances the humoral immune response to plasmid DNA-encoded antigens." Vaccine. Feb. 28, 2001; 19(15-16):1911-23.

Hartikka, J., et al. An improved plasmid DNA expression vector for direct injection into skeletal muscle, Hum Gene Ther. 1996 7:1205-1217.

Heppell., et al. Fish and Shellfish Immunology. 1998 8(4):271-286.

Horn NA., et al. "Cancer gene therapy using plasmid DNA: purification of DNA for human clinical trials." Hum Gene Ther. May 1995; 6(5):565-73.

Horton HM., et al. "IL-2 plasmid therapy of murine ovarian carcinoma inhibits the growth of tumor ascites and alters its cytokine profile." J Immunol. Dec. 15, 1999;163(12):6378-85.

(Continued)

*Primary Examiner* — Janet Epps-Smith
(74) *Attorney, Agent, or Firm* — Sughrue Mion, PLLC

(57) ABSTRACT

The disclosure provides adjuvants, immunogenic compositions, and methods useful for vaccination and immune response. In particular, the disclosure provides a class of adjuvants comprising cationic lipid:co-lipid mixtures and methods for delivering formulated compositions.

11 Claims, 18 Drawing Sheets

(56) References Cited

OTHER PUBLICATIONS

Ishii N., et al. "Cationic liposomes are a strong adjuvant for a DNA vaccine of human immunodeficiency virus type 1." AIDS Res Hum Retroviruses. Nov. 1, 1997;13(16):1421-8.
Jimenez GS., et al. Vaxfectin-formulated influenza DNA vaccines encoding NP and M2 viral proteins protect mice against lethal viral challenge, Hum Vaccin. 2007 3:157-164.
Karmali PP., et al. "Cationic liposomes as non-viral carriers of gene medicines: resolved issues, open questions, and future promises." Medicinal Research Reviews SEA. 2007 27(5):696-722.
Klavinskis LS., et al, "Intranasal immunization with plasmid DNA-lipid complexes elicits mucosal immunity in the female genital and rectal tracts." J Immunol. Jan. 1, 1999; 162(1):254-62.
Klavinskis LS., et al. "Mucosal immunization with DNA-liposome complexes." Vaccine. Jun. 1997; 15(8):818-20.
Leamy., et al. "Comparison of rabbit and mouse models for persistence analysis of plasmid-based vaccines." Hum Vaccine. 2006 2(3):113-118.
Lodmell., et al. "DNA immunization protects nonhuman primates against rabies virus." Nat med. 1998 4(8):949-952.
Manthorpe M., et al. "Plasmid vaccines and therapeutics: from design to applications." Advances in Biochemical Engineering, Biotechnology. 2005 99(1):41-92.
Niculescu-Duvaz D., et al. "Structure-activity relationship in cationic lipid mediated gene transfection." Current Medicinal Chemistry. 2003 10(14):1233-1261.
Menger, F.M., et al.,"Lipid-catalyzed transport of copper (II) through liquid membranes", J Organic Chem 58(7):1909-1916 (1993).
Norman., et al. in Methods in Molecular Medicine, vol. 9; DNA Vaccines: Methods and Protocols. D.B. Lowrie and R. Whalen, eds., 1999 Chapter 16, pp. 185-196.
Okada E., et al. "Intranasal immunization of a DNA vaccine with IL-12- and granulocyte-macrophage colony-stimulating factor (GM-CSF)-expressing plasmids in liposomes induces strong mucosal and cell-mediated immune responses against HIV-1 antigens." J Immunol. Oct. 1, 1997;159(7):3638-47.
Qin YJ., et al. "Gene suture—a novel method for intramuscular gene transfer and its application in hypertension therapy." Life Sci. 1999;65(21):2193-203.
Sasaki S., et al. "Adjuvant effect of Ubenimex on a DNA vaccine for HIV-1." Clin Exp Immunol. Jan. 1998;111(1):30-5.
Sasaki S., et al. "Monophosphoryl lipid A enhances both humoral and cell-mediated immune responses to DNA vaccination against human immunodeficiency virus type 1." Infect Immun. Sep. 1997;65(9):3520-8.
Sasaki S., et al. "Induction of systemic and mucosal immune responses to human immunodeficiency virus type 1 by a DNA vaccine formulated with QS-21 saponin adjuvant via intramuscular and intranasal routes." J Virol. Jun. 1998; 72(6):4931-9.
Selinsky., et al. "A DNA-based vaccine for the prevention of human cytomegalovirus-associated diseases." Hum Vaccine. 2005 1(1):16-23.
Slifka MK., et al. "Long-lived plasma cells: a mechanism for maintaining persistent antibody production." Curr Opin Immunol. Jun. 1998; 10(3):252-8.
Slifka MK., et al. "Bone marrow is a major site of long-term antibody production after acute viral infection." J Virol. Mar. 1995;69(3):1895-902.
Stephen DJ., et al. "A new cationic liposome DNA complex enhances the efficiency of arterial gene transfer in vivo." Hum Gene Ther. Oct. 1, 1996; 7(15):1803-12.
Ulmer JB., et al. "DNA vaccines." Curr Opin Immunol. Aug. 1996; 8(4):531-6.
Ulmer JB., et al. "Heterologous protection against influenza by injection of DNA encoding a viral protein." Science. 1993, 259(5102) 1745-1749.
Vahlsing HL., et al. "Immunization with plasmid DNA using a pneumatic gun." J Immunol Methods. Sep. 30, 1994; 175(1):11-22.
Vanderzanden L., et al. "DNA vaccines expressing either the GP or NP genes of Ebola virus protect mice from lethal challenge." Virology. Jun. 20, 1998;246(1):134-44.
Vilalta A., et al. "II. Cationic lipid-formulated plasmid DNA-based *Bacillus anthracis* vaccine: evaluation of plasmid DNA persistence and integration potential." Hum Gene Ther. Oct. 2005;16(10):1151-6.

Wang B., et al. "Mucosal immunization with a DNA vaccine induces immune responses against HIV-1 at a mucosal site." Vaccine. Jun. 1997; 15(8):821-5.

Wheeler CJ., et al. "A novel cationic lipid greatly enhances plasmid DNA delivery and expression in mouse lung." Proc Natl Acad Sci USA. 1996 93(1):11454-11459.

Wheeler CJ., et al. "Converting an alcohol to an amine in a cationic lipid dramatically alters to co-lipid requirement, cellular transfection activity and the ultrastructure of DNA-cytofectin complexes." Biochimica Et Biophysica Acta. 1996 1280(1):1-11.

Yokoyama M., et al. "DNA immunization: effects of vehicle and route of administration on the induction of protective antiviral immunity." Jul. 1996; 14(4):221-30.

Majeti, et al., "Enhanced intravenous transgeneexpression in mouse lung using cyclic-head cationic lipids." Chemistry &Biology ,11(4):427-437 (2004).

Agadjanyan, et al. "DNA plasmid based vaccination against the oncogenic human T cell leukemia virus type 1" Curr Top Microbiol Immunol. 1998 226:175-192.

Altman-Hamamdzic, et al. "Expression of beta-galactosidase in mouse brain: utilization of a novel nonreplicative Sindbis virus vector as a neuronal gene delivery system." Gene Ther. Aug. 1997;4(8):815-22.

Bins, et al. "A rapid and potent DNA vaccination strategy defined by in vivo monitoring of antigen expression." Nat Med. Aug. 2005; 11(8):899-904.

Boyer JD., et al. "In vivo protective anti-HIV immune responses in non-human primates through DNA immunization." J Med Primatol. Jun. 1996; 25(3):242-50.

Boyer JD., et al. "Protection of chimpanzees from high-dose heterologous HIV-1 challenge by DNA vaccination." Nat Med. May 1997;3(5):473.

Brunel F., et al. "Cationic lipid DC-Chol induces an improved and balanced immunity able to overcome the unresponsiveness to the hepatitis B vaccine." Vaccine. Apr. 23, 1999;17(17):2192-203.

Davis HL., et al. "DNA-based immunization against hepatitis B surface antigen (HBsAg) in normal and HBsAg-transgenic mice." Vaccine. 1997 15(8):849-852.

Debruyne LA., et al. "Lipid-mediated gene transfer of viral IL-10 prolongs vascularized cardiac allograft survival by inhibiting donor-specific cellular and humoral immune responses." Gene Ther. Aug. 1998;5(8):1079-87.

Doh SG., et al. "Spatial-temporal patterns of gene expression in mouse skeletal muscle after injection of IacZ plasmid DNA." Gene Ther. Jul. 1997; 4(7):648-63.

Dow SW., et al. "Lipid-DNA complexes induce potent activation of innate immune responses and antitumor activity when administered intravenously." J Immunol. Aug. 1, 1999;163(3):1552-61.

Etchart N., et al. "Class I-restricted CTL induction by mucosal immunization with naked DNA encoding measles virus haemagglutinin." J Gen Virol. Jul. 1997; 78 ( Pt 7):1577-80.

* cited by examiner

SEQUENCE LISTING

```
<160> NUMBER OF SEQ ID NOS: 5

<210> SEQ ID NO 1
<211> LENGTH: 23
<212> TYPE: PRT
<213> ORGANISM: Artificial Sequence
<220> FEATURE:
<223> OTHER INFORMATION: M2 consensus sequence

<400> SEQUENCE: 1

Met Ser Leu Leu Thr Glu Val Glu Thr Pro Arg Ile Asn Glu Trp Gly
1               5                   10                  15

Cys Arg Cys Asn Asp Ser Ser
            20

<210> SEQ ID NO 2
<211> LENGTH: 9
<212> TYPE: PRT
<213> ORGANISM: Artificial Sequence
<220> FEATURE:
<223> OTHER INFORMATION: NP class I peptide

<400> SEQUENCE: 2

Thr Tyr Gln Arg Thr Arg Ala Leu Val
1               5

<210> SEQ ID NO 3
<211> LENGTH: 23
<212> TYPE: PRT
<213> ORGANISM: Artificial Sequence
<220> FEATURE:
<223> OTHER INFORMATION: NP class II peptide

<400> SEQUENCE: 3

Phe Trp Arg Gly Glu Asn Gly Lys Thr Arg Ser Ala Tyr Glu Arg Met
1               5                   10                  15

Cys Asn Ile Leu Lys Gly Lys
            20

<210> SEQ ID NO 4
<211> LENGTH: 24
<212> TYPE: PRT
<213> ORGANISM: Artificial Sequence
<220> FEATURE:
<223> OTHER INFORMATION: NP class II peptide

<400> SEQUENCE: 4
```

```
Ala Val Lys Gly Val Gly Thr Met Val Met Glu Leu Ile Arg Met Ile
1               5                   10                  15

Lys Arg Gly Ile Asn Asp Arg Asn
            20

<210> SEQ ID NO 5
<211> LENGTH: 23
<212> TYPE: PRT
<213> ORGANISM: Artificial Sequence
<220> FEATURE:
<223> OTHER INFORMATION: NP class II peptide

<400> SEQUENCE: 5

Arg Leu Ile Gln Asn Ser Leu Thr Ile Glu Arg Met Val Leu Ser Ala
1               5                   10                  15

Phe Asp Glu Arg Arg Asn Lys
            20
```

COMPOSITIONS AND METHODS FOR ENHANCING IMMUNE RESPONSES TO VACCINES

CROSS REFERENCE TO OTHER APPLICATIONS

This application is a continuation application of U.S. patent application Ser. No. 13/566,892, filed Aug. 3, 2012, currently pending, which is a divisional application of U.S. patent application Ser. No. 13/243,692, filed Sep. 23, 2011, now abandoned, which is a divisional application of U.S. patent application Ser. No. 12/126,787, filed May 23, 2008, now abandoned, which claims priority benefit under 35 U.S.C. §119(e) to U.S. Provisional Patent Application No. 60/939,702, filed May 23, 2007; and U.S. Provisional Patent Application No. 61/044,338, filed Apr. 11, 2008, the disclosure of each are hereby incorporated by reference in their entirety for all purposes. This application also incorporates by reference the following documents: U.S. patent application Ser. No. 08/097,266, filed on Jul. 23, 1993, now U.S. Pat. No. 5,399,163; U.S. patent application Ser. No. 07/920,106, filed Jul. 24, 1992, now U.S. Pat. No. 5,383,851; and U.S. patent application Ser. No. 09/937,604, filed Sep. 26, 2001, now U.S. Pat. No. 7,105,574.

FIELD OF THE DISCLOSURE

The disclosure provides cationic-lipids and their use as adjuvants, immunogenic compositions, and methods useful for vaccination. The disclosure also provides compounds, compositions and methods useful for enhancing immune responses, especially the humoral immune response of vertebrates to vaccines. In particular, the disclosure provides adjuvant compositions of cytofectin:co-lipid mixtures, wherein the cytofectin is a compound of formula I or II, including (±)-N-(3-aminopropyl)-N,N-dimethyl-2,3-bis(syn-9-tetradeceneyloxy)-1-propanaminium bromide (GAP-DMORIE). Also disclosed are adjuvant compositions wherein the adjuvant is GAP-DMORIE, and the co-lipid is 1,2-diphytanoyl-sn-glycero-3-phosphoethanolamine (DPyPE), i.e., the Vaxfectin® adjuvant.

BACKGROUND OF THE DISCLOSURE

In the late 1980s, it was discovered that direct intramuscular (i.m.) injection of lipid-DNA complexes results in measurable protein expression, and that "naked" plasmid DNA (pDNA) is taken up and expressed in muscle to a greater extent than lipid-DNA complexes (Feigner, Scientific American, 276(6), 102-106 (1997)). Later, it was shown that cationic lipid-protein mixtures afforded greater immune responses after i.m. injection than protein alone (Brunel, Vaccine 17, 2192-2203 (1999).

One of the first applications of pDNA injection technology was the induction of an immune response. In 1991, it was first reported that mice could be immunized against HIV gp120 by i.m. vaccination with gp120 plasmid DNA (Feigner et al., Nature, 349, 351-352 (1991)), and that mice could be protected from a lethal challenge of influenza virus after DNA immunization with influenza nucleoprotein (NP) antigen. Protection obtained after immunization with the highly conserved NP antigen extended across 2 different viral strains (Ulmer et al., Current Opinions In Immunology, 8, 531-536 (1996)). Numerous publications in the field of polynucleotide-based vaccination followed thereafter (e.g., Boyer et al., J. Med, Primatology, 25(3), 242-250 (1996); Boyer et al., Nature Medicine, 3(5), 526-532 (1997); Davis et al., Vaccine, 15(8), 849-852 (1997); Wang et al., Vaccine, 15(8), 821-825 (1997); Agadjanyan et al., Current Topics In Microbiology And Immunology, 226, 175-192 (1998); Heppell et al., Fish & Shellfish Immunology, 8(4), 271-286 (1998); Lodmell et al., Nature Medicine, 4(8), 949-952 (1998); Vanderzanden et al., Virology, 246(1), 134-144 (1998)).

A major problem frequently encountered in the course of polynucleotide-based vaccination is insufficient or suboptimal humoral response. Often, the antigens or immunogens encoded by the polynucleotide are expressed in vivo, but they are not sufficiently immunogenic to raise the antibody titer in the organism to sufficient levels to provide protection against subsequent challenge and/or to maintain the potential for generating therapeutically active antibody levels over extended time periods. To obtain a stronger humoral and/or cellular response, it is common to administer such vaccines in an immunogenic composition containing an adjuvant, a material which enhances the immune response of the patient to the vaccine. Adjuvants are useful generally for improving the immune response of an organism to a particular immunogen and are commonly included in vaccine compositions to increase the amount of antibodies produced and/or to reduce the quantity of immunogen and the frequency of administration.

A variety of adjuvants have been reported to effect differing levels of immune response enhancement to polynucleotide-based vaccination. Examples of such adjuvant materials include semi-synthetic bacterial cell wall-derived monophosphoryl lipid A (Sasaki, S., et al., Infection and Immunity 65(9), 3250-3258 (1997)), small molecule immunostimulators (Sasaki, S., et al., Clin. Exp. Immunol, 111, 30-35 (1998)), and saponins (Sasaki, S., et al., J. Virology 72(6), 4391-4939 (1998)). The immune response from i.m. pDNA vaccination has also been enhanced through the use of cationic lipids (Ishii, N., et al., Aids Res. Hum. Retroviruses 13(16), 1421-1428 (1997)), Okada, E., et al., J Immunology 159, 3638-3647 (1997); Yokoyama, M., et al., FEMS Immunol. Med. Microbiol. 14, 221-230 (1996); Gregoriadis, G., et al., FEBS Letters 402, 107-110 (1997); Gramzinski, R. A., et al., Molecular Medicine 4, 109-118 (1998); Klavinskis, L. S., et al., Vaccine 15(8), 818-820 (1997); Klavinskis, L. S., et al., J. Immunology 162, 254-262 (1999); Etchart, N., et al., J. Gen. Virology 78, 1577-1580 (1997); Norman, J., et al., in Methods in Molecular Medicine, Vol. 29; DNA Vaccines: Methods and Protocols, D. B. Lowrie and R. Whalen, eds., Chapter 17, pp. 185-196 (1999)). Cationic lipids were originally studied to enhance delivery of pDNA into cells in vitro; however, further development has led to successful specific applications of protein delivery in vivo (Wheeler, C. J., et al., Proc. Nail. Acad. Sci, USA 93, 11454-11459 (1996); Stephan, D. J., et al., Human Gene Therapy 7, 1803-1812 (1996); DeBruyne, L. A., et al., Gene Therapy 5, 1079-1087 (1998)). Accordingly, such cationic lipids may be useful for vaccine applications by enhancing delivery of the pDNA into the cells responsible for giving rise to the humoral arm of the immune response, thereby increasing antibody titer levels.

Commonly used adjuvants, such as Alum, show low levels of immune response enhancement for vaccination (typically less than 3-fold) and possess undesirable toxicological and manufacturing profiles. In addition, cationic lipids used previously for vaccination show only low levels of humoral enhancement. Thus, there is a need for more adjuvant compositions useful for enhancing the immune response of vertebrates to immunization, especially to pDNA vaccination.

BRIEF SUMMARY OF THE DISCLOSURE

The present disclosure provides compounds, adjuvant and immunogenic compositions, and methods of using these compounds and compositions for the vaccination of a vertebrate, to help protect the vertebrate from a disease, to treat a diseased vertebrate, or both. More specifically the present disclosure provides a class of cationic lipids that are useful for enhancing the immune response of vertebrates to immunization, especially in response to pDNA, polypeptide, peptide, nucleic acid, polysaccharide, or inactivated (protein-based) vaccines derived from whole virus particle vaccination.

In certain embodiments, the present disclosure provides methods for immunizing a vertebrate by administering to the vertebrate a composition comprising a polynucleotide that encodes for an immunogen, wherein the polynucleotide is complexed with an adjuvant composition comprising a cationic lipid compound of formula I or

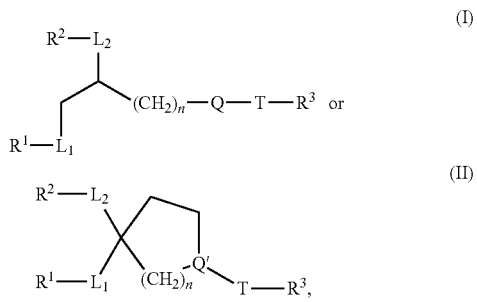

or an enantiomer, diastereomer, or a pharmaceutically acceptable salt or solvate thereof, wherein $R^1$, $R^2$, $R^3$, $L_1$, $L_2$, $Q$, $Q'$ and $T$ are as described herein, one or more counter ions, and one or more co-lipids.

In other embodiments, the composition comprises one or more co-lipids. The immunogen-encoding polynucleotide, upon incorporation into the cells of the vertebrate, produces an immunologically effective amount of an immunogen (e.g., an immunogenic protein). The adjuvant composition of the present disclosure enhances the immune response of the vertebrate to the immunogen.

In another aspect, the present disclosure provides adjuvant compositions comprising a mixture of one or more cationic lipid compounds and one or more co-lipids, which adjuvant composition is useful for enhancing the humoral immune response of a vertebrate to an immunogen. In some embodiments, the adjuvant composition comprises the cationic lipid compound of formula I or II, and one or more co-lipids. In other embodiments, the co-lipid is a neutral lipid such as, for example, a phosphatidylethanolamine including but not limited to 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycero-3-phosphoethanolamine (DMPE), or a dialkylglycerol such as 1,2-di-O-phytanyl-sn-glycerol (DPyG) or a zwitterionic co-lipid such as DPyRIE carboxylate, or diphytanoylphosphatidylglycerol.

In another aspect, the present disclosure provides immunogenic compositions comprising one or more immunogens and an adjuvant composition comprising the cationic lipid compound of formula I or II, and one or more co-lipids. In certain embodiments, the source of the immunogen is an immunogen-encoding polynucleotide, such as in the case of a pDNA vaccine. In some embodiments, the pDNA or polynucleotide may be complexed with an adjuvant composition comprising the cationic lipid compound of formula I or II, and one or more co-lipids.

In another aspect, the present disclosure provides methods for immunizing a vertebrate by administering to the vertebrate an immunogenic composition comprising a complex of one or more immunogen-encoding polynucleotides and the cationic lipid compound of formula I or II in an amount sufficient to generate an immune response to the encoded immunogen. In some embodiments, the immunogenic composition further includes one or more co-lipids such as, for example, DOPE and/or DPyPE.

The present disclosure further provides compositions and methods useful for enhancing the humoral immune response of a vertebrate to a polynucleotide-based vaccine, through the use of the compounds of formula I or II. Elevation of antibody levels is particularly advantageous in applications where antibody levels from the immunogen-encoding polynucleotide alone are sub-optimal. In a related advantage, if the desired level of antibodies is produced with a given dose of pDNA, the amount of pDNA necessary to reach the predetermined antibody titer level can be reached using a lower pDNA dose. For pDNA vaccination applications, this advantage is important because acceptable vaccination volumes, coupled with functional limits on the concentration of pDNA, define an upper limit on a given vaccine dose. This advantage is particularly beneficial for vaccines containing multiple plasmids, each of which must be present in sufficient quantity to elicit an immune response to its particular transgene.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the Drawings:

FIG. 2 consists of three graphs (2A, 2B and 2C) comparing humoral immune responses obtained in rabbits with unformulated pDNA vaccine injected IM with needle & syringe, or delivered either IM or ID with a needle-free injection device Biojector® 2000 (B2000), to Vaxfectie-formulated vaccine delivered either IM or ID with Biojector®2000.

FIG. 2A shows anti-gB geometric mean titers (GMT) obtained three weeks after a single injection, whereas

DETAILED DESCRIPTION OF THE DISCLOSURE

Figure 1:
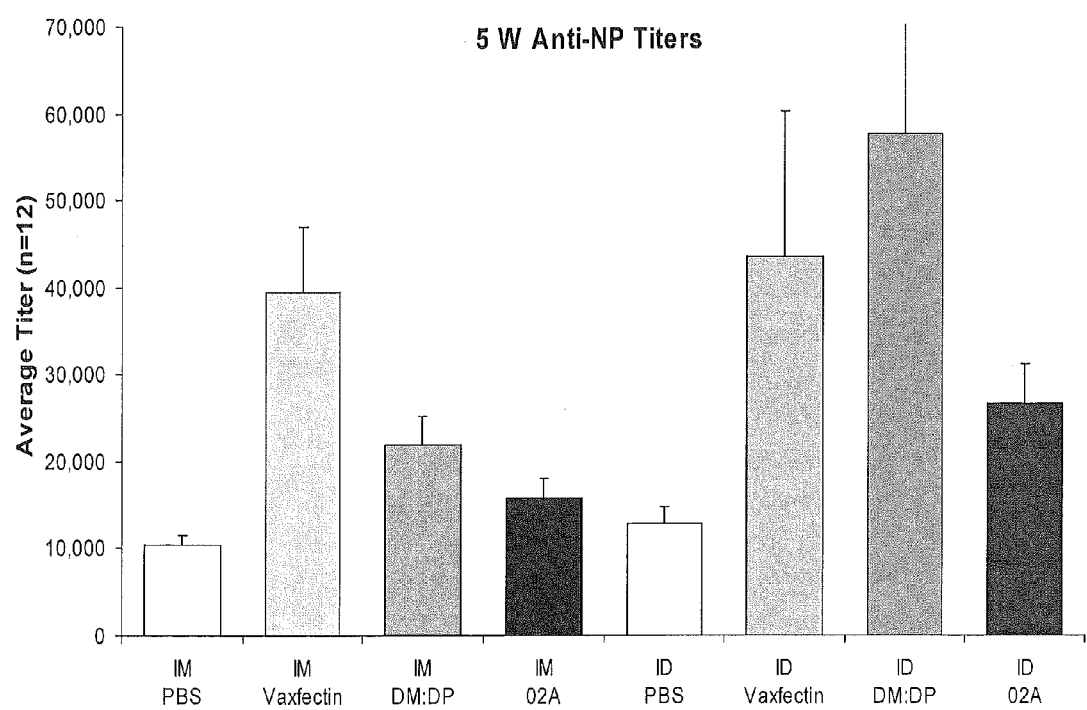
FIG. 1 is a bar graph illustrating enhanced humoral immune responses obtained with cytofectin:co-lipid vaccine formulations delivered either IM or ID with needle & syringe.

It will be apparent to one skilled in the art, in view of the following detailed description and the claims appended hereto, that various substitutions and modifications may be made to the present disclosure without departing from the scope of the disclosure.

DEFINITIONS

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH—CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R' or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkyl" or "cycloalkylalkyl" also refers to a 3 to 7 membered cycloalkyl group attached to the remainder of the molecule via an unsubstituted alkylene group. Recitation of a specific number of carbon atoms (e.g., $C_1$-$C_{10}$ cycloalkylalkyl) refers to the number of carbon atoms in the alkylene group.

The term "heterocycloalkyl" or "heterocycloalkylalkyl" also refers to a 3 to 7 membered heterocycloalkyl group attached to the remainder of the molecule via an unsubstituted alkylene group. Recitation of a specific number of carbon atoms (e.g., $C_1$-$C_{10}$ hetero-cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical, R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro($C_1$-$C_4$)alkyl, in a number ranging from zero to the total number of open valences on aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR)$_n$—X'—(C"R''')$_d$—, where s and d are independently integers of from 0 to 3, and X' is —O—, —NR'—, —S—, —S(O)—, —S(O)

$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques.

When the compounds described herein contain olefinic bonds or other centers of geometric asymmetry, and unless specified otherwise, it is intended that the compounds include both E and Z geometric isomers.

Where two groups are "optionally joined together to form a ring," the two groups are covalently bonded together with the atom or atoms to which the two groups are joined to form a substituted or unsubstituted aryl, a substituted or unsubstituted heteroaryl, a substituted or unsubstituted cycloalkyl, or a substituted or unsubstituted heterocycloalkyl ring.

The terms "arylalkyl," "heteroarylalkyl," "cycloalkyl-alkyl," and "heterocycloalkyl-alkyl," as used herein, refer to an aryl, heteroaryl, cycloalkyl and heterocycloalkyl, respectively, attached to the remainder of the molecule via an alkylene group. Where an "arylalkyl," "heteroarylalkyl," "cycloalkyl-alkyl," or "heterocycloalkyl-alkyl" is substituted, one or more substituent moieties may be covalently bonded to the alkylene moiety and/or the aryl, heteroaryl, cycloalkyl and heterocycloalkyl moieties, respectively. A "$C_1$-$C_{20}$" arylalkyl, heteroarylalkyl, cycloalkyl-alkyl, or heterocycloalkyl-alkyl, are moieties in which a $C_1$-$C_{20}$ alkylene links an aryl, heteroaryl, $C_4$-$C_8$ cycloalkyl, and 4 to 8 membered heterocycloalkyl, respectively, to the remainder of the molecule. A "$C_1$-$C_8$" arylalkyl, heteroarylalkyl, cycloalkyl-alkyl, or heterocycloalkyl-alkyl, are moieties in which a $C_1$-$C_8$ alkylene links an aryl, heteroaryl, $C_5$-$C_7$ cycloalkyl, and 5 to 7 membered heterocycloalkyl, respectively, to the remainder of the molecule.

A "substituent group," as used herein, means a group selected from the following moieties:

(A) —OH, —NH$_2$, —SH, —CN, —CF$_3$, oxy, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxy, —OH, —NH$_2$, —SH, —CF$_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "higher alkyl" refers to those alkyl groups having at least six carbon atoms. The term "lower alkyl" refers to those alkyl groups having from one to five carbon atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

In addition to salt forms, the present disclosure relates to compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The term "treating" refers to any indicia of success in the treatment, amelioration or prevention of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment, amelioration or prevention of symptoms can be based on objective or subjective parameters; including the results of a physical examination, neuropsychiatric exams, and/or a psychiatric evaluation.

The symbol ⌇ denotes the point of attachment of a moiety to the remainder of the molecule.

Cationic Lipid Compounds of Formula I and Formula II

The present disclosure is directed to the polynucleotide-based and polypeptide-based immunization of a vertebrate, to protect from or treat a vertebrate with a disease condition. The present disclosure includes the use of cationic lipids, especially the cationic lipid compound of formula I or II in adjuvants, immunogenic compositions, and methods for immunizing a vertebrate, especially with polynucleotude-based immunogen.

The adjuvant composition of the present disclosure includes one or more cationic lipids and, in some embodiments, one or more co-lipids. In one embodiment, the cationic lipid is a compound of formula I or II:

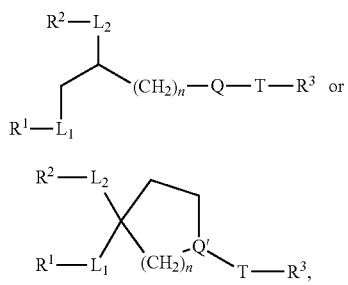

(I)

(II)

wherein $R^1$, $R^2$, $R^3$, $L_1$, $L_2$, Q, Q' and T are as described below.

In one aspect, the disclosure provides compounds having formula I:

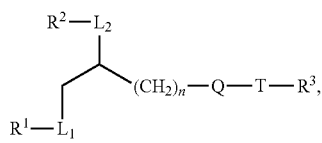

(I)

or an enantiomer, diastereomer, or a pharmaceutically acceptable salt or solvate thereof, wherein:

$R^1$ and $R^2$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^1$ and $R^2$ are each optionally independently substituted with 1 to 5 $R^{16}$ groups;

$L_1$ and $L_2$ are each independently a direct bond, O, NH, N($C_1$-$C_6$ alkyl), or S(O)$_m$, wherein m is an integer from 0 to 2;

n is an integer from 0 to 6;

Q is independently —$Z_1N^+Z_2$— or —$Z_1P^+Z_2$—;

$Z_1$ and $Z_2$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or substituted or unsubstituted —(CH$_2$)$_m$—$R^3$ wherein m is an integer from 1 to 6, and wherein $Z_1$ and $Z_2$ are each optionally independently substituted with 1 to 5 $R^{16}$ groups;

T is substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl; wherein Q is optionally independently substituted with 1 to 5 $R^{16}$ groups; and $R^3$ is independently —OR$^4$, —S(O)$_m$R$^5$, —NR$^6$R$^7$, —N$^+$R$^8$R$^9$R$^{10}$, —PR$^{11}$R$^{12}$, or —P$^+$R$^{13}$R$^{14}$R$^{15}$;

$R^4$ and $R^5$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^4$ and $R^5$ are each optionally independently substituted with 1 to 5 $R^{16}$ groups;

$R^6$ and $R^7$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^6$ and $R^7$, together with the N atom to which they are attached, form substituted or unsubstituted heteroaryl or substituted or unsubstituted heterocycloalkyl, wherein $R^6$ and $R^7$ are each optionally independently substituted with 1 to 5 $R^{16}$ groups;

$R^8$, $R^9$ and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, or $R^8$ is as described, and $R^9$ and $R^{10}$, together with the N atom to which they are attached, form substituted or unsubstituted heteroaryl or substituted or unsubstituted heterocycloalkyl, wherein $R^8$, $R^9$ and $R^{10}$ are each optionally independently substituted with 1 to 5 $R^{16}$ groups;

$R^{11}$, $R^{12}$ and $R^{13}$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^{11}$ is as described, and $R^{12}$ and $R^{13}$, together with the P atom to which they are attached, form substituted or unsubstituted heterocycloalkyl, wherein $R^{11}$, $R^{12}$ and $R^{13}$ are each optionally independently substituted with 1 to 5 $R^{16}$ groups;

$R^{16}$ is hydrogen, halogen, nitro, cyano, hydroxyl, alkyl, cycloalkyl, perfluoroalkyl, heteroalkyl, heterocycloalkyl, aryl, arylalkyl, heteroaryl, heteroarylalkyl, —(CH$_2$)$_j$CN, —(CH$_2$)$_j$OR$^{17}$, —(CH$_2$)$_j$C(O)R$^{17}$, —(CH$_2$)$_j$C(O)OR$^{17}$, —(CH$_2$)$_j$NR$^{18}$R$^{19}$, —(CH$_2$)$_j$C(O)NR$^{18}$R$^{19}$, —(CH$_2$)$_j$C(O) NR$^{18}$R$^{19}$, —(CH$_2$)$_j$NR$^{20}$C(O)R$^{17}$, —(CH$_2$)$_j$NR$^{20}$C(O) OR$^{17}$, —(CH$_2$)$_j$N$^{20}$C(O)NR$^{18}$R$^{19}$, —(CH$_2$)$_j$S(O)$_m$R$^{21}$, —(CH$_2$)$_j$S(O)$_2$NR$^{18}$R$^{19}$, or —(CH$_2$)$_j$NR$^{20}$S(O)$_2$R$^{21}$, wherein each j is independently an integer from 0 to 6, and each m is independently an integer from 0 to 2;

$R^{17}$, $R^{18}$, $R^{19}$, $R^{20}$ and $R^{21}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{17}$, $R^{20}$ and $R^{21}$ are as described above, and $R^{18}$ and $R^{19}$, together with the N atom to which they are attached, form substituted or unsubstituted heteroaryl, or substituted or unsubstituted heterocycloalkyl;

with the proviso that the compound of formula I is not GAP-DMORIE; and one or more counter ions.

In another aspect, the disclosure provides an adjuvant composition comprising a mixture of one or more cationic lipids having formula I:

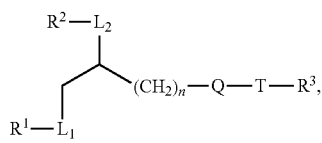

(I)

or an enantiomer, diastereomer, or a pharmaceutically acceptable salt or solvate thereof, wherein:

$R^1$ and $R^2$ are each independently substituted or unsubstituted alkyl (includes alkenyl and alkynyl), substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^1$ and $R^2$ are each optionally independently substituted with 1 to 5 $R^{16}$ groups;

$L_1$ and $L_2$ are each independently a direct bond, O, NH, $N(C_1-C_6$ alkyl), Se, Te, or $S(O)_m$, wherein m is an integer from 0 to 2;

n is an integer from 0 to 6;

Q is independently —$Z_1N^+Z_2$— or —$Z_1P^+Z_2$—;

$Z_1$ and $Z_2$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or substituted or unsubstituted —$(CH_2)_m$—$R^3$ wherein m is an integer from 1 to 6, and wherein $Z_1$ and $Z_2$ are each optionally independently substituted with 1 to 5 $R^{16}$ groups;

T is substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl; wherein Q is optionally independently substituted with 1 to 5 $R^{16}$ groups; and $R^3$ is independently —$OR^4$, —$S(O)_mR^5$, —$NR^6R^7$, —$N^+R^8R^9R^{10}$, —$PR^{11}R^{12}$, or —$P^+R^{13}R^{14}R^{15}$;

$R^4$ and $R^5$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^4$ and $R^5$ are each optionally independently substituted with 1 to 5 $R^{16}$ groups;

$R^6$ and $R^7$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^6$ and $R^7$, together with the N atom to which they are attached, form substituted or unsubstituted heteroaryl or substituted or unsubstituted heterocycloalkyl, wherein $R^6$ and $R^7$ are each optionally independently substituted with 1 to 5 $R^{16}$ groups;

$R^8$, $R^9$ and $R^{19}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, or $R^8$ is as described, and $R^9$ and $R^{19}$, together with the N atom to which they are attached, form substituted or unsubstituted heteroaryl or substituted or unsubstituted heterocycloalkyl, wherein $R^8$, $R^9$ and $R^{19}$ are each optionally independently substituted with 1 to 5 $R^{16}$ groups;

$R^{11}$, $R^{12}$ and $R^{13}$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^{11}$ is as described, and $R^{12}$ and $R^{13}$, together with the P atom to which they are attached, form substituted or unsubstituted heterocycloalkyl, wherein $R^{11}$, $R^{12}$ and $R^{13}$ are each optionally independently substituted with 1 to 5 $R^{16}$ groups;

$R^{16}$ is hydrogen, halogen, nitro, cyano, hydroxyl, alkyl, cycloalkyl, perfluoroalkyl, heteroalkyl, heterocycloalkyl, aryl, arylalkyl, heteroaryl, heteroarylalkyl, —$(CH_2)_jCN$, —$(CH_2)_jOR^{17}$, —$(CH_2)_jC(O)R^{12}$, —$(CH_2)_jC(O)OR^{17}$, —$(CH_2)_jNR^{18}R^{19}$, —$(CH_2)_jC(O)NR^{18}R^{19}$, —$(CH_2)_jC(O)NR^{18}R^{19}$, —$(CH_2)_jNR^{20}C(O)R^{17}$, —$(CH_2)_jNR^{20}C(O)OR^{17}$, —$(CH_2)_jN^{20}C(O)NR^{18}R^{19}$, —$(CH_2)_jS(O)_mR^{21}$, —$(CH_2)_jS(O)_2NR^{18}R^{19}$, or —$(CH_2)_jNR^{20}S(O)_2R^{21}$, wherein each j is independently an integer from 0 to 6, and each m is independently an integer from 0 to 2;

with the proviso that the compound of formula I is not GAP-DMORIE;

one or more counter ions, and one or more co-lipids.

In another aspect, the disclosure provides an adjuvant composition, wherein:

$R^1$ and $R^2$ are each independently substituted or unsubstituted alkyl, substituted or unsubstituted alkenyl, or substituted or unsubstituted alkynyl;

$L_1$ and $L_2$ are each independently O or NH;

n is 1; and

Q is independently —$Z_1N^+Z_2$—.

In another aspect, the disclosure provides an adjuvant composition, wherein $R^1$ and $R^2$ are each independently substituted or unsubstituted $(C_1-C_{20})$alkyl, substituted or unsubstituted $(C_2-C_{20})$alkenyl, or substituted or unsubstituted $(C_2-C_{20})$alkynyl.

In another aspect, the disclosure provides an adjuvant composition, wherein $R^1$ and $R^2$ are each independently:

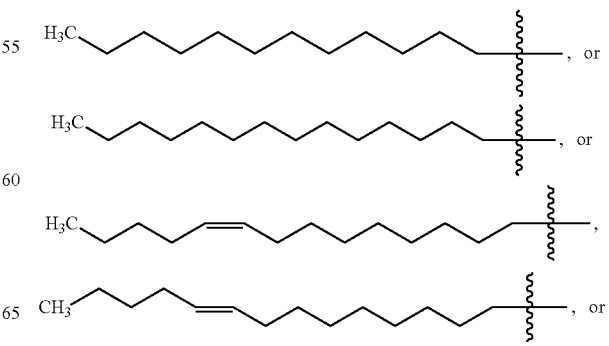

-continued

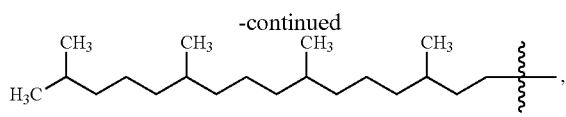

In another aspect, the disclosure provides an adjuvant composition, wherein:
$Z_1$ and $Z_2$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl; and
T is substituted or unsubstituted alkyl.

In another aspect, the disclosure provides an adjuvant composition, wherein:
$Z_1$ and $Z_2$ are each independently $(C_1-C_6)$alkyl; and
T is independently $(C_1-C_6)$alkyl.

In another aspect, the disclosure provides an adjuvant composition, wherein:
$Z_1$ and $Z_2$ are each independently substituted or unsubstituted $-(CH_2)_m-R^3$;
T is substituted or unsubstituted alkyl; and
$R^3$ is independently $-NR^6R^7$ or $-N^+R^8R^9R^{10}$.

In another aspect, the disclosure provides an adjuvant composition, wherein:
T is independently $(C_1-C_6)$alkyl;
$R^3$ is independently $-NR^6R^7$; and
$R^6$ and $R^7$ are each independently substituted or unsubstituted alkyl, substituted or unsubstituted heteroalkyl, or $R^6$ and $R^7$, together with the N atom to which they are attached, form substituted or unsubstituted heteroaryl or substituted or unsubstituted heterocycloalkyl.

In another aspect, the disclosure provides an adjuvant composition, wherein $R^6$ and $R^7$ are each independently substituted or unsubstituted $(C_1-C_6)$alkyl.

In another aspect, the disclosure provides an adjuvant composition, wherein $R^6$ and $R^7$, together with the N atom to which they are attached, form substituted or unsubstituted pyrrolyl, substituted or unsubstituted imidazolyl, substituted or unsubstituted pyrrolidinyl, substituted or unsubstituted pyrazolinyl, substituted or unsubstituted piperidinyl, substituted or unsubstituted piperazinyl, substituted or unsubstituted morpholinyl, or substituted or unsubstituted thiomorpholinyl.

In another aspect, the disclosure provides an adjuvant composition, wherein:
T is independently $(C_1-C_6)$alkyl;
$R^3$ is independently $-N^+R^8R^9R^{10}$; and
$R^8$, $R^9$ and $R^{10}$ are each independently substituted or unsubstituted alkyl, substituted or unsubstituted heteroalkyl, or $R^8$ is as described, and $R^9$ and $R^{10}$, together with the N atom to which they are attached, form substituted or unsubstituted heteroaryl or substituted or unsubstituted heterocycloalkyl.

In another aspect, the disclosure provides an adjuvant composition, wherein $R^8$, $R^9$ and $R^{10}$ are each independently substituted or unsubstituted $(C_1-C_6)$alkyl.

In another aspect, the disclosure provides an adjuvant composition, wherein $R^9$ and $R^{10}$, together with the N atom to which they are attached, form substituted or unsubstituted pyrrolyl, substituted or unsubstituted imidazolyl, substituted or unsubstituted pyrrolidinyl, substituted or unsubstituted pyrazolinyl, substituted or unsubstituted piperidinyl, substituted or unsubstituted piperazinyl, substituted or unsubstituted morpholinyl, or substituted or unsubstituted thiomorpholinyl.

In another aspect, the disclosure provides an adjuvant composition, wherein the counter ion is negatively charged.

In another aspect, the disclosure provides an adjuvant composition, wherein the negatively charged counter ion is $F^-$, $Cl^-$, $Br^-$, $I^-$, $CH_3COO^-$, $CF_3COO^-$ In another aspect, the disclosure provides an adjuvant composition, wherein the co-lipid is a neutral lipid.

In another aspect, the disclosure provides an adjuvant composition, wherein the neutral lipid is a phosphatidylethanolamine, and/or a phosphatidylcholine, and/or a mono-, di-, or trialkylglycerol, and/or a mono-, di-, or triacylglycerol, and/or a zwitterionic co-lipid such as DPyRIE carboxylate, or phosphatidylinositol, fatty acid, mono-, di-, or triacylglycerol, lysophosphatidyl-ethanolamine, lysophosphatidylcholine In another aspect, the disclosure provides an adjuvant composition, wherein the phosphatidylethanolamine is 1,2-dioleoyl-sn-glycero-3-phosphoethanolamine (DOPE) and/or 1,2-diphytanoyl-sn-glycero-3-phosphoethanolamine (DPyPE), and/or 1,2-dimyristoyl-glycero-3-phosphoethanolamine (DMPE).

In another aspect, the disclosure provides an adjuvant composition, wherein the phosphatidylethanolamine is 1,2-diphytanoyl-sn-glycero-3-phosphoethanolamine (DPyPE).

In another aspect, the disclosure provides an adjuvant composition, wherein the compound of formula I and the co-lipid ratio is from about 9:1 to about 1:9.

In another aspect, the disclosure provides an adjuvant composition, wherein the compound of formula I and the co-lipid are in molar ratio of from about 4:1 to about 1:4.

In another aspect, the disclosure provides an adjuvant composition, wherein the compound of formula I and the co-lipid are in molar ratio of from about 2:1 to about 1:2.

In another aspect, the disclosure provides an adjuvant composition, wherein the compound of formula I and the co-lipid are in molar ratio of about 1:1.

In another aspect, the disclosure provides an adjuvant composition, wherein the compound of formula I and DPyPE are in molar ratio of from about 2:1 to about 1:2.

In another aspect, the disclosure provides an adjuvant composition, wherein the compound of formula I and DPyPE are in molar ratio of about 1:1.

In another aspect, the disclosure provides an adjuvant composition, wherein the compound of formula I has formulae:

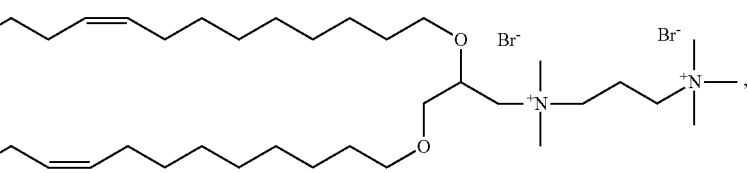

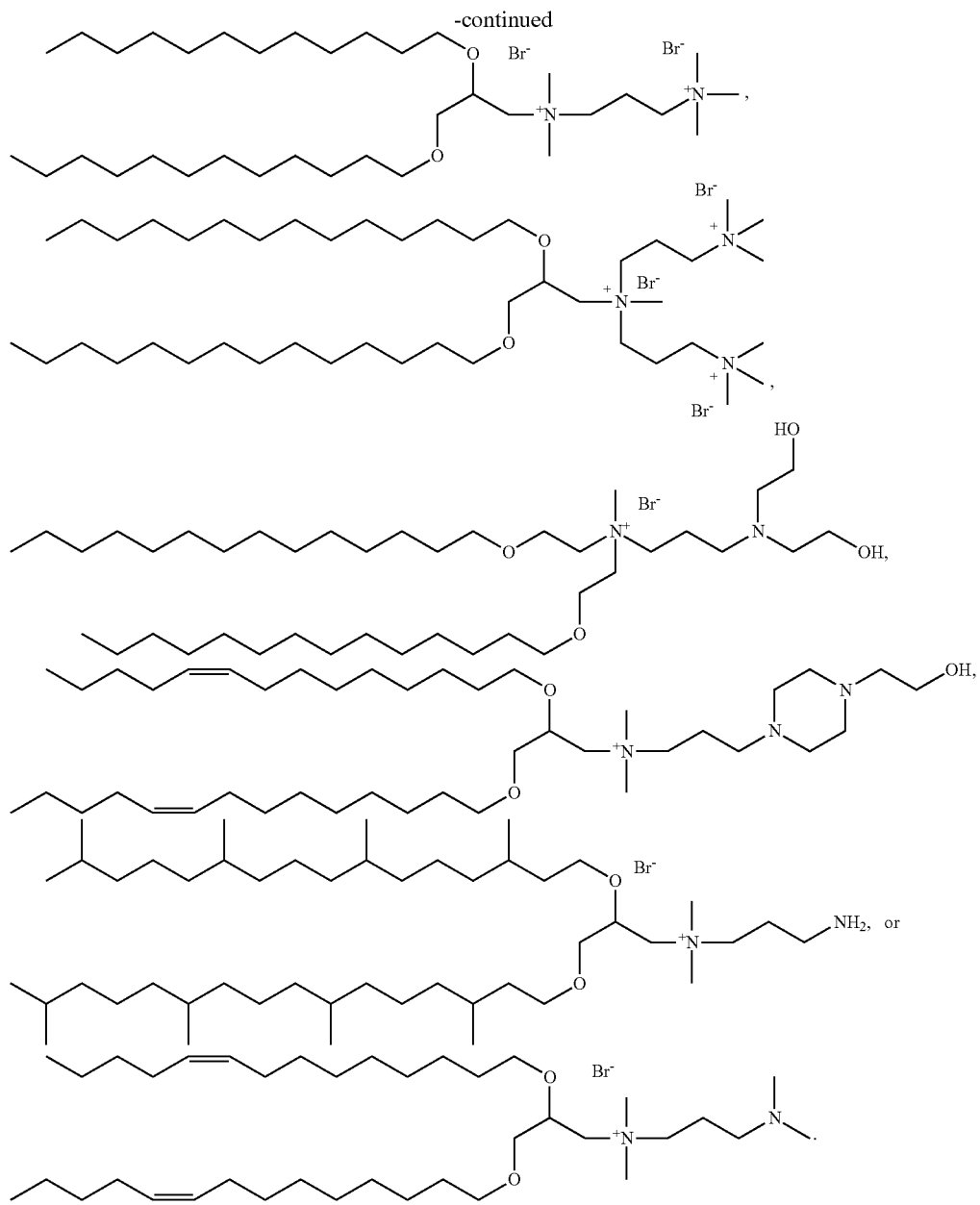

In another aspect, the disclosure provides methods for immunizing a vertebrate comprising administering into a tissue or cavity of the vertebrate an immunogenic composition comprising (a) one or more antigenic polypeptides, immunogenic polypeptides or polysaccharides in an amount sufficient to generate an immune response to the one or more antigenic polypeptides, immunogenic polypeptides or polysaccharides, and (b) the adjuvant compositions disclosed herein.

In another aspect, the disclosure provides methods for immunizing a vertebrate, wherein the immunogen-encoding polynucleotide, upon incorporation into the cells of the vertebrate, produces an immunologically effective amount of an immunogen (e.g., an immunogenic protein).

In another aspect, the disclosure provides methods for immunizing a vertebrate, wherein the adjuvant composition disclosed herein enhances the immune response of the vertebrate to the immunogen.

In another aspect, the disclosure provides immunogenic compositions comprising one or more immunogens and the adjuvant compositions disclosed herein.

In another aspect, the disclosure provides immunogenic compositions comprising one or more immunogens and the adjuvant compositions disclosed herein, wherein the immunogen is one or more antigenic polypeptides, immunogenic polypeptides, inactivate virus, attenuated virus or polysaccharides.

In another aspect, the disclosure provides immunogenic compositions comprising one or more immunogens and the adjuvant compositions disclosed herein, wherein the immunogen is an immunogen-encoding polynucleotide.

In another aspect, the disclosure provides immunogenic compositions comprising one or more immunogens and the adjuvant compositions disclosed herein, wherein the immunogen-encoding polynucleotide is in a pDNA vaccine.

In another aspect, the disclosure provides methods for immunizing a vertebrate comprising administering to the vertebrate an immunogenic composition comprising a complex of one or more immunogen-encoding polynucleotides and the adjuvant composition disclosed herein, in an amount sufficient to generate an immune response to the encoded immunogen.

In another aspect, the disclosure provides methods for immunizing a vertebrate, wherein the immunogenic composition further comprises one or more co-lipids, including mono-, di-, and triacyl amphiphiles and mono-, di-, and trialkyl amphiphiles, such as fatty acids, monoacyl-, monoalkylglycerol, lysophospholipids and mono- and diacylglycerol, diacylphospholipids, and trialkyl or triacyl glycerol.

In another aspect, the disclosure provides methods for immunizing a vertebrate, wherein the one or more co-lipids is DOPE, DPyPE, or DPyG.

In another aspect, the disclosure provides methods for providing a mammal a prophylactic or therapeutic treatment associated with a bacterial infection comprising: administering to the mammal an immunogenic composition comprising (a) one or more antigenic polypeptides, immunogenic polypeptides or polysaccharides associated with the bacterial infection in an amount sufficient to generate an immune response to the one or more antigenic polypeptides, immunogenic polypeptides or polysaccharides, and (b) the adjuvant composition disclosed herein. The antigenic polypeptides can be free in solution or derivatized with a hydrophobic moiety, such as an acyl chain, to facilitate association with the adjuvant.

In another aspect, the disclosure provides methods for providing a mammal a prophylactic or therapeutic treatment associated with a viral infection comprising: administering to the mammal an immunogenic composition comprising (a) one or more antigenic polypeptides, immunogenic polypeptides, inactivate virus, attenuated virus or polysaccharides associated with the viral infection in an amount sufficient to generate an immune response to the one or more antigenic polypeptides, immunogenic polypeptides, inactivate virus, attenuated virus or polysaccharides, and (b) the adjuvant composition disclosed herein.

In another aspect, the disclosure provides methods for providing a mammal a prophylactic or therapeutic treatment associated with an abnormal growth of a cell population comprising: administering to the mammal an immunogenic composition comprising (a) one or more antigenic polypeptides, immunogenic polypeptides or polysaccharides associated with the abnormal growth of the cell population in an amount sufficient to generate an immune response to the one or more antigenic polypeptides, immunogenic polypeptides or polysaccharides, and (b) the adjuvant composition disclosed herein.

In another aspect, the disclosure provides pharmaceutical kits comprising: (a) a container holding one or more antigenic polypeptides, immunogenic polypeptides, inactivate virus, attenuated virus or polysaccharides, and (b) the adjuvant composition disclosed herein; wherein the one or more antigenic polypeptides, immunogenic polypeptides, inactivate virus, attenuated virus or polysaccharides is provided in a prophylactically or therapeutically effective amount to treat a vertebrate.

In another aspect, the disclosure provides compounds having formula II:

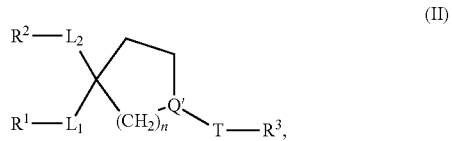

or an enantiomer, diastereomer, or a pharmaceutically acceptable salt or solvate thereof, wherein:

$R^1$ and $R^2$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^1$ and $R^2$ are each optionally independently substituted with 1 to 5 $R^{16}$ groups;

$L_1$ and $L_2$ are each independently a direct bond, O, NH, $N(C_1\text{-}C_6\text{ alkyl})$, or $S(O)_m$, wherein m is an integer from 0 to 2;

n is an integer from 1 to 3;

Q' is independently —$N^+Z_1$— or —$P^+Z_1$—;

$Z_1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or substituted or unsubstituted —$(CH_2)_m$—$R^3$ wherein m is an integer from 1 to 6, and wherein $Z_1$ is optionally independently substituted with 1 to 5 $R^{16}$ groups;

T is substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl; wherein T is optionally independently substituted with 1 to 5 $R^{16}$ groups; and $R^3$ is independently —$OR^4$, —$S(O)_mR^5$, —$NR^6R^7$, —$N^+R^8R^9R^{10}$, —$PR^{11}R^{12}$, or —$P^+R^{13}R^{14}R^{15}$;

$R^4$ and $R^5$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^4$ and $R^5$ are each optionally independently substituted with 1 to 5 $R^{16}$ groups;

$R^6$ and $R^7$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^6$ and $R^7$, together with the N atom to which they are attached, form substituted or unsubstituted heteroaryl or substituted or unsubstituted heterocycloalkyl, wherein $R^6$ and $R^7$ are each optionally independently substituted with 1 to 5 $R^{16}$ groups;

$R^8$, $R^9$ and $R^{19}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, or $R^8$ is as described, and $R^9$ and $R^{10}$, together with the N atom to which they are attached, form substituted or unsubstituted heteroaryl or substituted or unsubstituted heterocycloalkyl, wherein $R^8$, $R^9$ and $R^{19}$ are each optionally independently substituted with 1 to 5 $R^{16}$ groups;

$R^{11}$, $R^{12}$ and $R^{13}$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^{11}$ is as described, and $R^{12}$ and $R^{13}$, together with the P atom to which they are attached, form substituted or unsubstituted heterocycloalkyl, wherein $R^{11}$, $R^{12}$ and $R^{13}$ are each optionally independently substituted with 1 to 5 $R^{16}$ groups;

$R^{16}$ is hydrogen, halogen, nitro, cyano, hydroxyl, alkyl, cycloalkyl, perfluoroalkyl, heteroalkyl, heterocycloalkyl, aryl, arylalkyl, heteroaryl, heteroarylalkyl, —$(CH_2)_j$CN, —$(CH_2)_j$OR$^{17}$, —$(CH_2)_j$C(O)R$^{17}$, —$(CH_2)_j$C(O)OR$^{17}$, —$(CH_2)_j$NR$^{18}$R$^{19}$, —$(CH_2)_j$C(O)NR$^{18}$R$^{19}$, —$(CH_2)_j$OC(O)NR$^{18}$R$^{19}$, —$(CH_2)_j$NR$^{20}$C(O)R$^{17}$, —$(CH_2)_j$NR$^{20}$C(O)OR$^{17}$, —$(CH_2)_j$N$^{20}$C(O)NR$^{18}$R$^{19}$, —$(CH_2)_j$S(O)$_m$R$^{21}$, —$(CH_2)_j$S(O)$_2$NR$^{18}$R$^{19}$, or —$(CH_2)_j$NR$^{20}$S(O)$_2$R$^{21}$, wherein each j is independently an integer from 0 to 6, and each m is independently an integer from 0 to 2;

$R^{17}$, $R^{18}$, $R^{19}$, $R^{20}$ and $R^{21}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{17}$, $R^{20}$ and $R^{21}$ are as described above, and $R^{18}$ and $R^{19}$, together with the N atom to which they are attached, form substituted or unsubstituted heteroaryl, or substituted or unsubstituted heterocycloalkyl; and one or more counter ions.

In another aspect, the disclosure provides adjuvant compositions comprising a mixture of one or more cationic lipids having formula II:

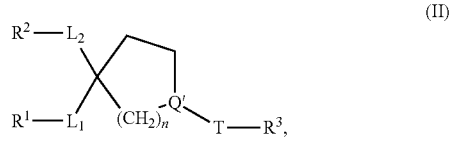

(II)

or an enantiomer, diastereomer, or a pharmaceutically acceptable salt or solvate thereof, wherein:

$R^1$ and $R^2$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^1$ and $R^2$ are each optionally independently substituted with 1 to 5 $R^{16}$ groups;

$L_1$ and $L_2$ are each independently a direct bond, O, NH, N($C_1$-$C_6$ alkyl), or S(O)$_m$, wherein m is an integer from 0 to 2;

n is an integer from 1 to 3;

Q' is independently —N$^+$Z$_1$— or —P$^+$Z$_1$—;

$Z_1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or substituted or unsubstituted —$(CH_2)_m$—R$^3$ wherein m is an integer from 1 to 6, and wherein $Z_1$ is optionally independently substituted with 1 to 5 $R^{16}$ groups;

T is substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl; wherein T is optionally independently substituted with 1 to 5 $R^{16}$ groups; and $R^3$ is independently —OR$^4$, —NR$^6$R$^7$, —N$^+$R$^8$R$^9$R$^{10}$, —PR$^{11}$R$^{12}$, or —P$^+$R$^{13}$R$^{14}$R$^{15}$;

$R^4$ and $R^5$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, wherein $R^4$ and $R^5$ are each optionally independently substituted with 1 to 5 $R^{16}$ groups;

$R^6$ and $R^7$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^6$ and $R^7$, together with the N atom to which they are attached, form substituted or unsubstituted heteroaryl or unsubstituted heterocycloalkyl, wherein $R^6$ and $R^7$ are each optionally independently substituted with 1 to 5 $R^{16}$ groups;

$R^8$, $R^9$ and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl, or $R^8$ is as described, and $R^9$ and $R^{10}$, together with the N atom to which they are attached, form substituted or unsubstituted heteroaryl or substituted or unsubstituted heterocycloalkyl, wherein $R^8$, $R^9$ and $R^{10}$ are each optionally independently substituted with 1 to 5 $R^{16}$ groups;

$R^{11}$, $R^{12}$ and $R^{13}$ are each independently substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, substituted or unsubstituted carboxyalkyl, or $R^{11}$ is as described, and $R^{12}$ and $R^{13}$, together with the P atom to which they are attached, form substituted or unsubstituted heterocycloalkyl, wherein $R^{11}$, $R^{12}$ and $R^{13}$ are each optionally independently substituted with 1 to 5 $R^{16}$ groups;

$R^{16}$ is hydrogen, halogen, nitro, cyano, hydroxyl, alkyl, cycloalkyl, perfluoroalkyl, heteroalkyl, heterocycloalkyl, aryl, arylalkyl, heteroaryl, heteroarylalkyl, —(CH$_2$)$_j$CN, —(CH$_2$)$_j$OR$^{17}$, —(CH$_2$)$_j$C(O)R$^{17}$, —(CH$_2$)$_j$C(O)OR$^{17}$, —(CH$_2$)$_j$NR$^{18}$R$^{19}$, —(CH$_2$)$_j$C(O)NR$^{18}$R$^{19}$, —(CH$_2$)$_j$OC(O)NR$^{18}$R$^{19}$, —(CH$_2$)$_j$NR$^{20}$C(O)R$^{17}$, —(CH$_2$)$_j$NR$^{20}$C(O)OR$^{17}$, —(CH$_2$)$_j$N$^{20}$C(O)NR$^{18}$R$^{19}$, —(CH$_2$)$_j$S(O)$_m$R$^{21}$, —(CH$_2$)$_j$S(O)$_2$NR$^{18}$R$^{19}$, or —(CH$_2$)$_j$NR$^{20}$S(O)$_2$R$^{21}$, wherein each j is independently an integer from 0 to 6, and each m is independently an integer from 0 to 2;

$R^{17}$, $R^{18}$, $R^{19}$, $R^{20}$ and $R^{21}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{17}$, $R^{20}$ and $R^{21}$ are as described above, and $R^{18}$ and $R^{19}$, together with the N atom to which they are attached, form substituted or unsubstituted heteroaryl, or substituted or unsubstituted heterocycloalkyl;
one or more counter ions; and
one or more co-lipids.

In another aspect, the disclosure provides adjuvant compositions comprising a mixture of one or more cationic lipids having formula II, wherein:

$R^1$ and $R^2$ are each independently substituted or unsubstituted alkyl, substituted or unsubstituted alkenyl, or substituted or unsubstituted alkynyl;
$L_1$ and $L_2$ are each independently O or NH;
n is 1; and
Q' is independently —$Z_1N^+Z_2$—.

In another aspect, the disclosure provides adjuvant compositions comprising a mixture of one or more cationic lipids having formula II, wherein $R^1$ and $R^2$ are each independently substituted or unsubstituted ($C_1$-$C_{20}$)alkyl, substituted or unsubstituted ($C_2$-$C_{20}$)alkenyl, or substituted or unsubstituted ($C_2$-$C_{20}$)alkynyl.

In another aspect, the disclosure provides adjuvant compositions comprising a mixture of one or more cationic lipids having formula II, wherein $R^1$ and $R^2$ are each independently:

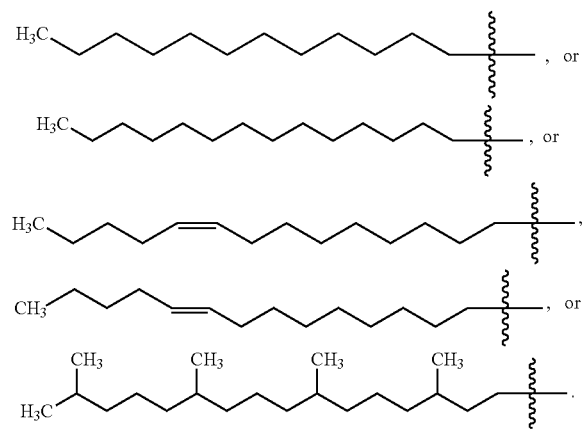

In another aspect, the disclosure provides adjuvant compositions comprising a mixture of one or more cationic lipids having formula II, wherein:

$Z_1$ and $Z_2$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, substituted or unsubstituted arylalkyl, substituted or unsubstituted heteroarylalkyl, or substituted or unsubstituted carboxyalkyl; and T is substituted or unsubstituted alkyl.

In another aspect, the disclosure provides adjuvant compositions comprising a mixture of one or more cationic lipids having formula II, wherein:

$Z_1$ and $Z_2$ are each independently ($C_1$-$C_6$)alkyl; and
T is independently ($C_1$-$C_6$)alkyl, In another aspect, the disclosure provides adjuvant compositions comprising a mixture of one or more cationic lipids having formula II, wherein:

$Z_1$ and $Z_2$ are each independently substituted or unsubstituted —(CH$_2$)$_m$—R$^3$;
T is substituted or unsubstituted alkyl; and
$R^3$ is independently —NR$^6$R$^7$ or —N$^+$R$^8$R$^9$R$^{10}$.

In another aspect, the disclosure provides adjuvant compositions comprising a mixture of one or more cationic lipids having formula II, wherein:

T is independently ($C_1$-$C_6$)alkyl;
$R^3$ is independently —NR$^6$R$^7$; and
$R^6$ and $R^7$ are each independently substituted or unsubstituted alkyl, substituted or unsubstituted heteroalkyl, or $R^6$ and $R^7$, together with the N atom to which they are attached, form substituted or unsubstituted heteroaryl or substituted or unsubstituted heterocycloalkyl.

In another aspect, the disclosure provides adjuvant compositions comprising a mixture of one or more cationic lipids having formula II, wherein $R^6$ and $R^7$ are each independently substituted or unsubstituted ($C_1$-$C_6$)alkyl.

In another aspect, the disclosure provides adjuvant compositions comprising a mixture of one or more cationic lipids having formula II, wherein $R^6$ and $R^7$, together with the N atom to which they are attached, form substituted or unsubstituted pyrrolyl, substituted or unsubstituted imidazolyl, substituted or unsubstituted pyrrolidinyl, substituted or unsubstituted pyrazolinyl, substituted or unsubstituted piperidinyl, substituted or unsubstituted piperazinyl, substituted or unsubstituted morpholinyl, or substituted or unsubstituted thiomorpholinyl.

In another aspect, the disclosure provides adjuvant compositions comprising a mixture of one or more cationic lipids having formula II, wherein:

T is independently ($C_1$-$C_6$)alkyl;
$R^3$ is independently —N$^+$R$^8$R$^9$R$^{10}$; and
$R^8$, $R^9$ and $R^{10}$ are each independently substituted or unsubstituted alkyl, substituted or unsubstituted heteroalkyl, or $R^8$ is as described, and $R^9$ and $R^{10}$, together with the N atom to which they are attached, form substituted or unsubstituted heteroaryl or substituted or unsubstituted heterocycloalkyl.

In another aspect, the disclosure provides adjuvant compositions comprising a mixture of one or more cationic lipids having formula II, wherein $R^8$, $R^9$ and $R^{10}$ are each independently substituted or unsubstituted ($C_1$-$C_6$)alkyl.

In another aspect, the disclosure provides adjuvant compositions comprising a mixture of one or more cationic lipids having formula II, wherein $R^9$ and $R^{10}$, together with the N atom to which they are attached, form substituted or unsubstituted pyrrolyl, substituted or unsubstituted imidazolyl, substituted or unsubstituted pyrrolidinyl, substituted or unsubstituted pyrazolinyl, substituted or unsubstituted piperidinyl, substituted or unsubstituted piperazinyl, substituted or unsubstituted morpholinyl, or substituted or unsubstituted thiomorpholinyl.

In another aspect, the disclosure provides adjuvant compositions comprising a mixture of one or more cationic lipids having formula II, wherein the counter ion is negatively charged.

In another aspect, the disclosure provides adjuvant compositions comprising a mixture of one or more cationic lipids having formula II, wherein the negatively charged counter ion is F⁻, Cl⁻, Br⁻, $CH_3CO^-$, or $CF_3COO^-$.

In another aspect, the disclosure provides adjuvant compositions comprising a mixture of one or more cationic lipids having formula II, wherein the co-lipid is a neutral lipid.

In another aspect, the disclosure provides adjuvant compositions comprising a mixture of one or more cationic lipids having formula II, wherein the neutral lipid is a phosphatidylethanolamine, and/or a phosphatidylcholine, and/or a mono-, di-, or trialkylglycerol, and/or a mono-, di, or triacylglycerol, and/or a non-phospholipid zwitterionic co-lipid.

In another aspect, the disclosure provides adjuvant compositions comprising a mixture of one or more cationic lipids having formula II, wherein the phosphatidylethanolamine is 1,2-dioleoyl-sn-glycero-3-phosphoethanolamine (DOPE) and/or 1,2-diphytanoyl-sn-glycero-3-phosphoethanolamine (DPyPE), and/or 1,2-dimyristoyl-glycero-3-phosphoethanolamine (DMPE).

In another aspect, the disclosure provides adjuvant compositions comprising a mixture of one or more cationic lipids having formula II, wherein the phosphatidyl-ethanolamine is 1,2-diphytanoyl-sn-glycero-3-phosphoethanolamine (DPyPE).

In another aspect, the disclosure provides adjuvant compositions comprising a mixture of one or more cationic lipids having formula II, wherein the compound of formula II and the co-lipid ratio is from about 9:1 to about 1:9.

In another aspect, the disclosure provides adjuvant compositions comprising a mixture of one or more cationic lipids having formula II, wherein the compound of formula II and the co-lipid are in molar ratio of from about 4:1 to about 1:4.

In another aspect, the disclosure provides adjuvant compositions comprising a mixture of one or more cationic lipids having formula II, wherein the compound of formula II and the co-lipid are in molar ratio of from about 2:1 to about 1:2.

In another aspect, the disclosure provides adjuvant compositions comprising a mixture of one or more cationic lipids having formula II, wherein the compound of formula II and the co-lipid are in molar ratio of about 1:1.

In another aspect, the disclosure provides adjuvant compositions comprising a mixture of one or more cationic lipids having formula II, wherein the compound of formula II and DPyPE are in molar ratio of from about 2:1 to about 1:2.

In another aspect, the disclosure provides adjuvant compositions comprising a mixture of one or more cationic lipids having formula II, wherein the compound of formula II and DPyPE are in molar ratio of about 1:1.

In another aspect, the disclosure provides adjuvant compositions comprising a mixture of one or more cationic lipids having formula II, wherein the compound of formula II has formula:

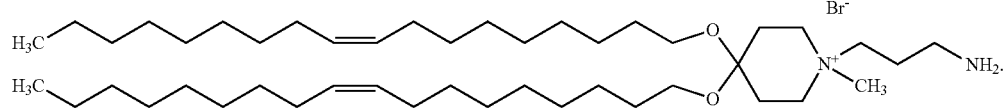 [SMILES: [Br-] ; CCCCCCCC/C=C\CCCCCCCCOC1(OCCCCCCCC/C=C\CCCCCCCC)CC[N+](C)(CCCN)CC1]

In another aspect, the disclosure provides methods for immunizing a vertebrate comprising administering into a tissue or cavity of the vertebrate an immunogenic composition comprising (a) one or more antigenic polypeptides, immunogenic polypeptides, inactivate virus, attenuated virus or polysaccharides in an amount sufficient to generate an immune response to the one or more antigenic polypeptides, immunogenic polypeptides, inactivate virus, attenuated virus or polysaccharides, and (b) the adjuvant compositions disclosed herein.

In another aspect, the disclosure provides methods for immunizing a vertebrate comprising administering into a tissue or cavity of the vertebrate an immunogenic composition, wherein the immunogen-encoding polynucleotide, upon incorporation into the cells of the vertebrate, produces an immunologically effective amount of an immunogen (e.g., an immunogenic protein).

In another aspect, the disclosure provides methods for immunizing a vertebrate comprising administering into a tissue or cavity of the vertebrate an immunogenic composition, wherein the adjuvant compositions disclosed herein enhances the immune response of the vertebrate to the immunogen.

In another aspect, the disclosure provides an immunogenic composition comprising one or more immunogens and the adjuvant compositions disclosed herein.

In another aspect, the disclosure provides an immunogenic composition comprising one or more immunogens and the adjuvant compositions disclosed herein, wherein the immunogen is one or more antigenic polypeptides, immunogenic polypeptides, inactivate virus, attenuated virus or polysaccharides.

In another aspect, the disclosure provides an immunogenic composition comprising one or more immunogens and the adjuvant compositions disclosed herein, wherein the immunogen is an immunogen-encoding polynucleotide.

In another aspect, the disclosure provides an immunogenic composition comprising one or more immunogens and the adjuvant compositions disclosed herein, wherein the immunogen-encoding polynucleotide is in a pDNA vaccine.

In another aspect, the disclosure provides methods for immunizing a vertebrate comprising administering to the vertebrate an immunogenic composition comprising a complex of one or more immunogen-encoding polynucleotides and the adjuvant composition disclosed herein, in an amount sufficient to generate an immune response to the encoded immunogen.

In another aspect, the disclosure provides methods for immunizing a vertebrate comprising administering to the vertebrate an immunogenic composition comprising a complex of one or more immunogen-encoding polynucleotides and the adjuvant composition disclosed herein, wherein the immunogenic composition further comprises one or more co-lipids, including mono-, di-, and triacyl amphiphiles and mono-, di-, and trialkyl amphiphiles, such as fatty acids, monoacyl-, monoalkylglycerol, lysophospholipids and mono- and diacylglycerol, diacylphospholipids, and trialkyl or triacyl glycerol.

In another aspect, the disclosure provides methods for immunizing a vertebrate comprising administering to the vertebrate an immunogenic composition comprising a complex of one or more immunogen-encoding polynucleotides and the adjuvant composition disclosed herein, wherein the one or more co-lipids is DOPE, DPyPE, and/or DPyG In another aspect, the disclosure provides methods for providing a mammal a prophylactic or therapeutic treatment associated with a bacterial infection comprising: administering to the mammal an immunogenic composition comprising (a) one or more antigenic polypeptides, immunogenic polypeptides or polysaccharides associated with the bacterial infection in an amount sufficient to generate an immune response to the one or more antigenic polypeptides, immunogenic polypeptides or polysaccharides, and (b) the adjuvant composition disclosed herein.

In another aspect, the disclosure provides methods for providing a mammal a prophylactic or therapeutic treatment associated with a viral infection comprising: administering to the mammal an immunogenic composition comprising (a) one or more antigenic polypeptides, immunogenic polypeptides, inactivate virus, attenuated virus or polysaccharides associated with the viral infection in an amount sufficient to generate an immune response to the one or more antigenic polypeptides, immunogenic polypeptides, inactivate virus, attenuated virus or polysaccharides, and (b) the adjuvant composition disclosed herein.

In another aspect, the disclosure provides methods for providing a mammal a prophylactic or therapeutic treatment associated with an abnormal growth of a cell population comprising: administering to the mammal an immunogenic composition comprising (a) one or more antigenic polypeptides, immunogenic polypeptides or polysaccharides associated with the abnormal growth of the cell population in an amount sufficient to generate an immune response to the one or more antigenic polypeptides, immunogenic polypeptides or polysaccharides, and (b) the adjuvant composition disclosed herein.

In another aspect, the disclosure provides pharmaceutical kits comprising: (a) a container holding one or more antigenic polypeptides, immunogenic polypeptides or polysaccharides, and (b) the adjuvant composition disclosed herein; wherein the one or more antigenic polypeptides, immunogenic polypeptides or polysaccharides is provided in a prophylactically or therapeutically effective amount to treat a vertebrate. The antigenic polypeptides can be free in solution or derivatized with a hydrophobic moiety, such as an acyl chain, to facilitate association with the adjuvant.

The primary amine of GAP-DMORIE is chemically active and has the potential to react with the ester of the helper lipid, or the phosphate of the DNA upon long term storage. This can result in inactivating the transfection complex, resulting in a reduction in the shelf life of the product. Surprisingly, hypermethylating the amine eliminates the chemical reactivity but does not affect the adjuvant activity of the lipid. As is shown in the examples, dimethylation and trimethylation of the primary amine of GAP-DMORIE formulated with DPyPE in a 1:1 molar ratio and complexed to DNA in a 4:1 mol/mol ratio of DNA phosphate to cationic lipid yielded equivalent protection in a mouse influenza challenge model.

Primary amines are reactive nucleophiles. Long term storage of these primary amines in an aqueous media can produce chemical reactions that are detrimental to a product, potentially impacting product stability resulting in reduced shelf life. Chemical reactivity can be controlled by adding substituent groups, such as methyl group ($—CH_3$), that reduce chemical reactivity but maintain net charge. This later aspect of the modification is pertinent to development of cationic amphiphiles for delivery of DNA. DNA can hydrogen bond and/or ionically bond with cationic amphiphiles. These two types of bonds dictate the interaction of DNA with cationic amphiphile based formulation for gene transfer. Hence, reducing the reactivity of a positively charged primary amine through derivatization with substituents groups does not eliminate the ability of the phosphates from the DNA backbone to ion pair with the positively charged quaternary amines.

Development of genetic vaccines requires the addition of the cationic amphiphiles to achieve sufficient expression to produce an immune response. The cationic amphiphiles also possess the ability to activate the immune system, thus increasing the potency of the vaccine. The exact mechanism for how these cationic amphiphiles accomplish immune activation is unknown. Also unknown are the chemical structure requirements of the cationic amphiphiles to activate the immune response. These unknowns limit predictability of chemical modifications on immune activation.

In this embodiment, conversion of a primary amine to a secondary amine or tertiary amine did not eliminate the adjuvant activity of the cationic amphiphile GAP-DMORIE in that both molecules formulated with DPyPE and complexed to flu antigen expression DNA plasmids resulted in equivalent survival of mice compared to the unmodified GAP-DMORIE when exposed to a lethal dose of influenza virus. The trimethyl-GAP-DMORIE can have an increased product shelf life compared to the unmodified GAP-DMORIE due to the reduction in reactivity of the primary amine.

As used herein, the term "co-lipid" refers to any hydrophobic material that can be combined with the cationic lipid component, e.g., the compounds of formula I or II. The co-lipid of the present disclosure can be amphipathic lipids, zwitterionic lipids, and non-ionic neutral lipids. Amphipathic lipids include phospholipids, e.g., phosphatidylethanolamines and phosphatidylcholines. Non-phospholipid zwitterionic lipids include DPyRIE carboxylate or DMRIE carboxylate. Non-ionic neutral lipids include cholesterol and dialkylglycerols. In one embodiment, phosphatidylethanolamines include but are not limited to DOPE and DPyPE. DPyPE comprises two phytanoyl substituents incorporated into the diacylphosphatidylethanolamine skeleton.

According to the present disclosure, the cationic lipid compounds of formula I or II, and co-lipids may be mixed or combined in a number of ways to produce a variety of adjuvant compositions of non-covalently bonded macroscopic structures, e.g., liposomes, multilamellar vesicles, unilamellar vesicles, micelles, and simple films. These cationic lipids and co-lipids can be mixed in a variety of molar ratios. In one embodiment, the molar ratio for the compounds of formula I or II and co-lipid is from about 9:1 to about 1:9. In another embodiment, the molar ratio is from about 4:1 to about 1:4. In another embodiment, the molar ratio is from about 2:1 to about 1:2. In yet another embodiment, the molar ratio is about 1:1.

The cationic lipid compounds of formula I or II and co-lipids can be dissolved in a solvent to increase homogenity of the mixture. Suitable solvents include chloroform. For example, the cationic lipid compound of formula I or II can be mixed with one or more co-lipids in chloroform, the mixture is subsequently evaporated under vacuum to form a dried thin layer of film on the inner surface of a glass vessel, e.g., a rotovap round-bottomed flask. Such dried mixtures can be suspended in an aqueous solvent where the amphipathic lipid component molecules self-assemble into homogenous lipid vesicles. These lipid vesicles can subsequently be processed by any methods used in the art to have a selected mean diameter of uniform size prior to complexing with other entities, e.g., pDNA. The sonication of a lipid solution is described in Feigner et al., *Proc. Natl. Acad. Sci.* USA 84, 7413-7417 (1987) and in U.S. Pat. No. 5,264,618, the disclosure of which is incorporated herein by reference.

The adjuvant compositions of the present disclosure may also include additives such as hydrophobic and amphiphilic additives. For example, the adjuvant composition can include sterols, fatty acids, gangliosides, glycolipids, lipopeptides, liposaccharides, neobees, niosomes, prostaglandins or sphingolipids. The amount of additives included in the adjuvant may be any including from about 0.1 mol % to about 99.9 mol %, from about 1 mol % to about 50 mol %, and from about 2 mol % to about 25 mol %, relative to total amount of lipid. These additives can also be included in an immunogenic composition containing the adjuvant composition of the present disclosure.

The immunogenic composition of the present disclosure also includes an adjuvant composition as described above and an immunogen. An "immunogen" is meant to encompass any substance that when introduced into a vertebrate, developing or developed, generates an immune response. For example, an immunogen may be a polypeptide with an amino acid sequence having one or more epitopes or combinations of epitopes, and an immunogen-encoding polynucleotide. An immunogen-encoding polynucleotide may be part of a non-infectious and non-integrating linear expression cassette, or a circular or linearized plasmid containing a non-infectious and non-integrating polynucleotide. A non-infectious polynucleotide is a polynucleotide that does not infect vertebrate cells while a non-integrating polynucleotide does not integrate into the genome of vertebrate cells. A linearized plasmid is a plasmid that was previously circular but has been linearized, for example, by digestion with a restriction endonuclease. Alternatively, the linear DNA can be produced enzymatically by PCR. The immunogen-encoding polynucleotide may comprise a sequence that directs the secretion of a polypeptide. Examples of polypeptides include, but are not limited to, those derived from infectious agents such as bacteria, viruses, parasites, or fungi, allergens such as those from pet dander, plants, dust, and other environmental sources, as well as certain self polypeptides, for example, tumor-associated antigens or Amyloid Beta (Abeta) which is a 39-43 amino acid peptide that is the main constituent of amyloid plaques in the brains of Alzheimer's patients, or haptens, such as nicotine or cocaine derivatives used for drug abuse vaccines.

The immunogen-encoding polynucleotide is intended to encompass a singular "polynucleotide" as well as plural "polynucleotides," and refers to an isolated molecule or construct. The immunogen-encoding polynucleotides include nucleotide sequences, nucleic acids, nucleic acid oligomers, messenger RNA (mRNA), DNA (e.g., pDNAs, derivatives of pDNA, linear DNA or linear expression cassettes (LECs)), or fragments of any of thereof. The immunogen-encoding polynucleotides may be provided in linear, circular, e.g., plasmid, or branched form as well as double-stranded or single-stranded form. The immunogen-encoding polynucleotides may comprise a conventional phosphodiester bond or a non-conventional bond, e.g., an amide bond, such as found in peptide nucleic acids (PNA).

In addition, an "immunogen" is also meant to encompass any poly-saccharide material, protein subunits or protein fragments and inactivated (protein-based) vaccines derived from whole virus particles useful in generating immune response.

The immunogenic composition of the present disclosure can also be used to prevent or treat, i.e., cure, ameliorate, lessen the severity of, or prevent or reduce contagion of viral, bacterial, fungal, and parasitic infectious diseases, as well as to treat allergies.

In addition, the immunogenic composition of the present disclosure can be used to prevent or treat, i.e., cure, ameliorate, or lessen the severity of cancer including, but not limited to, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometirum, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia).

Examples of viral immunogens include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuramimidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuramimidase, paramyxovirus polypeptides, parvovirus polypeptides, pestivirus polypeptides, picoma virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial immunogens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumo-* coccus polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* Fl and V antigens.

Examples of fungal immunogens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite immunogens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite immunogens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyrne* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite immunogens include, but are not limited to, polypeptides (including protective antigens as well as allergens) from fleas; ticks, including hard ticks and soft ticks, flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of tumor-associated immunogens include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), HER2/neu, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Also included as immunogens of the present disclosure are fragments or variants of the foregoing polypeptides, and any combination of the foregoing polypeptides. Furthermore, expressible nucleotide sequences of each of the foregoing polypeptides including fragments and/or variants thereof are also included within the scope of the present disclosure. Additional polypeptides may be found, for example in *"Foundations in Microbiology,"* Talaro, et al., eds., McGraw-Hill Companies (October, 1998), Fields, et al., *"Virology,"* 3rd ed., Lippincott-Raven (1996), *"Biochemistry and Molecular Biology of Parasites,"* Marr, et al, eds., Academic Press (1995), and Deacon, J., *"Modern Mycology,"* Blackwell Science Inc (1997), which are incorporated herein by reference.

The form of immunogen-encoding polynucleotides depends in part on the desired kinetics and duration of expression. When long-term delivery of a protein encoded by a polynucleotide is desired, the preferred form is DNA. Alternatively, when short-term transgene protein delivery is desired, the preferred form is mRNA, since mRNA can be rapidly translated into polypeptide, however RNA may be degraded more quickly than DNA.

In one embodiment, the immunogen-encoding polynucleotide is RNA, e.g., messenger RNA (mRNA). Methods for introducing RNA sequences into mammalian cells is described in U.S. Pat. No. 5,580,859, the disclosure of which is incorporated herein by reference. A viral alpha vector, a non-infectious vector useful for administering RNA, may be used to introduce RNA into mammalian cells. Methods for the in vivo introduction of alpha viral vectors to mammalian tissues are described in Altman-Hamamdzic, S., et al., *Gene Therapy* 4, 815-822 (1997), the disclosure of which is incorporated herein by reference.

In one embodiment, the immunogen-encoding polynucleotide is DNA. In the case of DNA, a promoter is preferably operably linked to the nucleotide sequence encoding for the immunogen. The promoter can be a cell-specific promoter that directs substantial transcription of the DNA only in predetermined cells. Other transcription control elements, besides a promoter, can be included with the polynucleotide to direct cell-specific transcription of the DNA. An operable linkage is a linkage in which a polynucleotide encoding for an immunogenic molecule is connected to one or more regulatory sequences in such a way as to place expression of the immunogen under the influence or control of the regulatory sequence(s). Two DNA sequences (such as a coding sequence and a promoter region sequence linked to the 5' end of the coding sequence) are operably linked if induction of promoter function results in the transcription of mRNA encoding for the desired immunogen and if the nature of the linkage between the two DNA sequences does not (1) result in the introduction of a frame-shift mutation, (2) interfere with the ability of the expression regulatory sequences to direct the expression of the immunogen, or (3) interfere with the ability of the DNA template to be transcribed. Thus, a promoter region would be operably linked to a DNA sequence if the promoter was capable of effecting transcription of that DNA sequence.

The immunogen-encoding polynucleotide, e.g., pDNA, mRNA, polynucleotide or nucleic acid oligomer can be solubilized in any of various buffers prior to mixing or complexing with the adjuvant components, e.g., cationic lipids and co-lipids. Suitable buffers include phosphate buffered saline (PBS), normal saline, Tris buffer, and sodium phosphate. Insoluble polynucleotides can be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art.

According to the present disclosure, the immunogen-encoding polynucleotides can be complexed with the adjuvant compositions of the present disclosure by any means known in the art, e.g., by mixing a pDNA solution and a solution of cationic lipid/co-lipid liposomes. In one embodiment, the concentration of each of the constituent solutions is adjusted prior to mixing such that the desired final pDNA/cationic lipid:co-lipid ratio and the desired pDNA final concentration will be obtained upon mixing the two solutions. For example, if the desired final solution is to be physiological saline (0.9% weight/volume), both pDNA and cationic lipid:co-lipid liposomes are prepared in 0.9% saline and then simply mixed to produce the desired complex. The cationic lipid:co-lipid liposomes can be prepared by any means known in the art. For example, one can hydrate a thin film of the cationic lipid compound of formula I or II and co-lipid mixture in an appropriate volume of aqueous solvent by vortex mixing at ambient temperatures for about 1 minute. Preparation of a thin film of the cationic lipid and co-lipid mixture is known to a skilled artisan and can be prepared by any suitable techniques. For example, one can mix chloroform solutions of the individual components to generate an equimolar solute ratio and subsequently aliquot a desired volume of the solutions into a suitable container where the solvent can be removed by evaporation, e.g., first with a stream of dry, inert gas such as argon and then by high vacuum treatment.

The immunogenic composition of the present disclosure can be used to immunize a vertebrate. The term "vertebrate" is intended to encompass a singular "vertebrate" as well as plural "vertebrates", and comprises developing and developed mammalian and avian species, as well as fish. The method for immunizing a vertebrate includes administering to the vertebrate an immunogenic composition of the present disclosure in an amount sufficient to generate an immune response to the immunogen.

The immunogenic compositions of the present disclosure may be administered according to any of various methods known in the art. For example, U.S. Pat. No. 5,676,954 reports on the injection of genetic material, complexed with cationic lipid carriers, into mice. Also, U.S. Pat. Nos. 5,589,466, 5,693,622, 5,580,859, 5,703,055, and PCT international patent application PCT/US94/06069 (WO 94/29469), the disclosures of which are incorporated herein by reference, provide methods for delivering DNA-cationic lipid complexes to mammals.

Specifically, the immunogenic compositions of the present disclosure may be administered to any tissue of a vertebrate, including, but not limited to, muscle, skin, sub-cutaneous space, brain, lung, liver, spleen, bone marrow, thymus, heart, lymph, blood, bone, cartilage, mucosal tissue, pancreas, kidney, gall bladder, stomach, intestine, testis, ovary, uterus, vaginal tissue, rectum, nervous system, eye, gland, tongue and connective tissue. The immunogenic compositions of the disclosure may also be administered to a body cavity, including, but not limited to, the lung, mouth, nasal cavity, stomach, peritoneum, intestine, heart chamber, vein, artery, capillary, lymphatic, uterus, vagina, rectum, and ocular cavity.

The immunogenic compositions of the present disclosure may be administered by intramuscular (i.m.), intranasal (i.n.), topical, intradermal (i.d.), epidermal, tansdermal, transcutaneous or subcutaneous (s.c.) routes. Other suitable routes of administration include transdermal, intranasal, tattooing, inhalation, intratracheal, transmucosal (i.e., across a mucous membrane), intra-cavity (e.g., oral, vaginal, or rectal), intraocular, vaginal, rectal, intraperitoneal, intraintestinal and intravenous (i.v.) administration.

Any mode of administration can be used so long as the administration results in desired immune response. Administration means of the present disclosure include, but not limited to, microneedles, sonoporation, ionotophoresis, transdermal/transcutaneous delivery, microseeding (tattoo devises), needle injection, electroporation, catheter infusion, biolistic injectors, particle accelerators (i.e., "gene guns") or pneumatic "needleless" injectors—for example, Med-E-Jet (Vahlsing, H., et al., *J. Immunol. Methods* 171, 11-22 (1994)), Pigjet (Schrijver, R., et al., *Vaccine* 15, 1908-1916 (1997)), Biojector (Davis, H., et al., *Vaccine* 12, 1503-1509 (1994); Gramzinski, R., et al., *Mol. Med.* 4, 109-118 (1998)), AdvantaJet, Medijector, gelfoam sponge depots, other commercially available depot materials (e.g., hydrogels), osmotic pumps (e.g., Alza minipumps), oral or suppositorial solid (tablet or pill) pharmaceutical formulations, spray/inhalers, topical skin creams, patches, and decanting, use of polynucleotide coated suture (Qin et al., *Life Sciences* 65, 2193-2203 (1999)) or topical applications during surgery. In an embodiment, the mode of administration is intramuscular needle-based injection or intranasal application as an aqueous solution.

Determining an effective amount of an immunogenic composition depends upon a number of factors including, for example, the chemical structure and biological activity of the substance, the age and weight of the subject, and the route of administration. The precise amount, number of doses, and timing of doses can be readily determined by those skilled in the art.

In certain embodiments, the immunogenic composition is administered as a pharmaceutical composition. Such a pharmaceutical composition can be formulated according to known methods, whereby the substance to be delivered is combined with a pharmaceutically acceptable carrier vehicle. Suitable vehicles and their preparation are described, for example, in *Remington's Pharmaceutical Sciences*, $16^{th}$ Edition, A, Osol, ed., Mack Publishing Co., Easton, Pa. (1980), and *Remington's Pharmaceutical Sciences*, $19^{th}$ Edition, A. R. Gennaro, ed., Mack Publishing Co., Easton, Pa. (1995). The pharmaceutical composition can be formulated as an emulsion, gel, solution, suspension, lyophilized form, or any other form known in the art. In addition, the pharmaceutical composition can also contain pharmaceutically acceptable additives including, for example, diluents, binders, stabilizers, and preservatives. Administration of pharmaceutically acceptable salts of the polynucleotide constructs described herein is preferred. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like.

For aqueous pharmaceutical compositions used in vivo, use of sterile pyrogen-free water is preferred. Such formulations will contain an effective amount of the immunogenic composition together with a suitable amount of vehicle in order to prepare pharmaceutically acceptable compositions suitable for administration to a vertebrate.

The present disclosure also provides kits for use in delivering a polypeptide to a vertebrate. Each kit includes a container holding 1 ng to 30 mg of an immunogen-encoding polynucleotide which operably encodes an immunogen within vertebrate cells in vivo. Furthermore, each kit includes, in the same or in a different container, an adjuvant composition comprising a cationic lipid compound of formula I or II and a co-lipid. Any of components of the pharmaceutical kits can be provided in a single container or in multiple containers. In one embodiment, the kit includes from about 1 ng to about 30 mg of a immunogen-encoding polynucleotide. In another embodiment, the kit includes from about 100 ng to about 10 mg of a immunogen-encoding polynucleotide.

Any suitable container or containers may be used with pharmaceutical kits. Examples of containers include, but are not limited to, glass containers, plastic containers, or strips of plastic or paper.

Each of the pharmaceutical kits may further comprise an administration means. Means for administration include, but are not limited to syringes and needles, catheters, biolistic injectors, particle accelerators, i.e., "gene guns," pneumatic "needleless" injectors, gelfoam sponge depots, other commercially available depot materials, e.g., hydrojels, osmotic pumps, and decanting or topical applications during surgery (topical patch-such as those used for nicotine delivery-passive or active administration). Each of the pharmaceutical kits may further comprise sutures, e.g., coated with the immunogenic composition (Qin et al., *Life Sciences* (1999) 65:2193-2203).

The kit can further comprise an instruction sheet for administration of the composition to a vertebrate. The polynucleotide components of the pharmaceutical composition are preferably provided as a liquid solution or they may be provided in lyophilized form as a dried powder or a cake. If the polynucleotide is provided in lyophilized form, the dried powder or cake may also include any salts, entry enhancing agents, transfection facilitating agents, and additives of the pharmaceutical composition in dried form. Such a kit may further comprise a container with an exact amount of sterile pyrogen-free water, for precise reconstitution of the lyophilized components of the pharmaceutical composition.

The container in which the pharmaceutical composition is packaged prior to use can comprise a hermetically sealed container enclosing an amount of the lyophilized formulation or a solution containing the formulation suitable for a pharmaceutically effective dose thereof, or multiples of an effective dose. The pharmaceutical composition is packaged in a sterile container, and the hermetically sealed container is designed to preserve sterility of the pharmaceutical formulation until use. Optionally, the container can be associated with administration means and/or instruction for use.

Pharmaceutical Compositions and Administration

In another aspect, the present disclosure relates to pharmaceutical compositions including the cationic lipid compound of formula I or II, and a co-lipid in a mixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: *The Science and Practice of Pharmacy* ($20^{th}$ ed.) Lippincott, Williams & Wilkins (2000).

The compounds according to the disclosure are effective over a wide dosage range. For example, in the treatment of adult humans, dosages from 0.01 to 10,000 mg, from 0.5 to 1000 mg, from 1 to 500 mg per day, and from 5 to 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: *The Science and Practice of Pharmacy* ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: *The Science and Practice of Pharmacy* ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose, Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores, Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other anti-proliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this disclosure may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

Exemplary Syntheses

The compounds of the disclosure are synthesized by an appropriate combination of generally well known synthetic methods. Techniques useful in synthesizing the compounds of the disclosure are both readily apparent and accessible to those of skill in the relevant art. The discussion below is offered to illustrate certain of the diverse methods available for use in assembling the compounds of the disclosure. However, the discussion is not intended to define the scope of reactions or reaction sequences that are useful in preparing the compounds of the present disclosure. The compounds of this disclosure may be made by the procedures and techniques disclosed in the Examples section below, as well as by known organic synthesis techniques.

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., *Protective Groups in Organic Synthesis,* 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking or protecting groups include, for example:

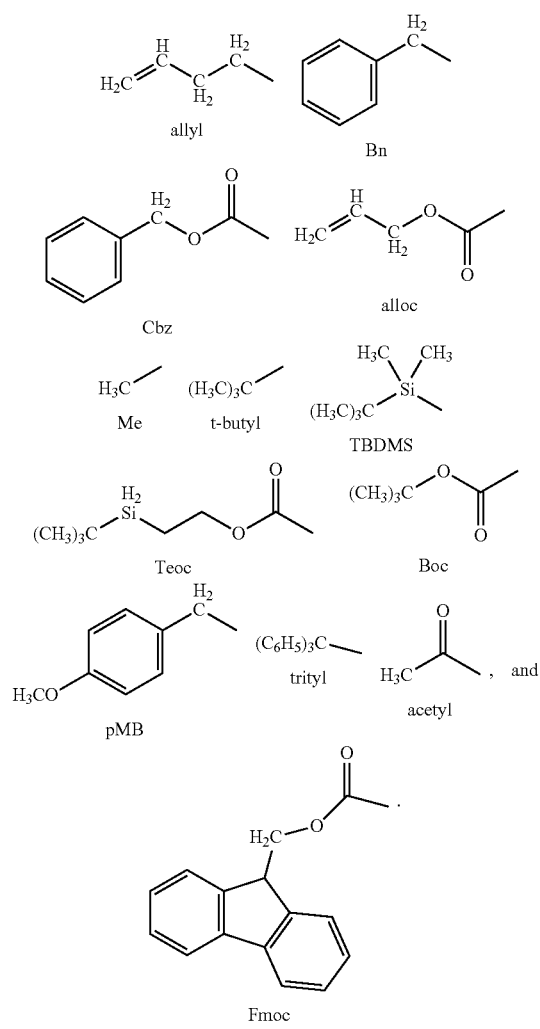

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. References cited throughout this application are examples of the level of skill in the art and are hereby incorporated by reference herein in their entirety for all purposes, whether previously specifically incorporated or not.

EXAMPLES

A. Synthesis of Compounds of the Present Invention

The following examples are offered to illustrate, but not to limit the claimed disclosure. The preparation of embodiments of the present disclosure is described in the following examples. Those of ordinary skill in the art will understand that the chemical reactions and synthesis methods provided may be modified to prepare many of the other compounds of the present disclosure. Where compounds of the present disclosure have not been exemplified, those of ordinary skill in the art will recognize that these compounds may be prepared by modifying synthesis methods presented herein, and by using synthesis methods known in the art.

Example I

Synthesis of (±)-N-(3-aminopropyl)-N,N-dimethyl-2,3-bis(myristoleyloxy)-1-propanaminium bromide (GAP-DMORIE, formula I)

Racemic 1-dimethylamino-2,3-propanediol (0.96 g; Janssen Chimica) was converted to the disodium salt in situ by treatment with sodium hydride (60% in oil, 0.8 g) in tetrahydrofuran (70 mL). Condensation with myristoleyl methane sulfonate (5.3 g; NuChek Prep) afforded crude (±)-N,N-dimethyl-(2,3-bis(myristoleyloxy))propylamine (DMOP-DMA). This material was purified to homogeneity by silica gel chromatography employing a step gradient of ether in hexane (from 10% to 50%), and finally neat ether, as the eluents. DMOP-DMA (2.4 g) was then treated with N-(3-bromopropyl)phthalimide (2.5 g) in dimethylformamide (15 mL) at elevated temperature (85° C., overnight) to effect quaternization of the amine. Removal of the dimethylformamide in vacuo followed by silica gel chromatography using a step gradient of methanol/chloroform as the eluent afforded TLC homogenous material. Deprotection of the primary amine was accomplished by treatment of the phthalimide (2.1 g) with anhydrous hydrazine (1.7 mL) in anhydrous ethanol (40 mL) and propargyl alcohol (10 eq.). Filtration, evaporative removal of the solvent, basic extraction (0.1 M NaOH), alumina chromatography, and washing with 1 M NaBr afforded the pure product.

Example II

Synthesis of (±)-N-(3'-N'-propyl-N',N',N'-trimethylammonium)-N,N-dimethyl-2,3-bis(myristoleyloxy)-1-propanaminium dibromide (Trimethyl-GAP-DMORIE, formula I)

GAP-DMORIE (0.64 g) was treated with 1 M NaOH (4.2 mL) and CH$_3$I (3 mL) in methanol (20 mL) at 0° C. to room temperature overnight to effect quaternization of the primary amine. The solvent was removed in vacuo, and the residue was taken up in $CHCl_3$ and washed with water. The organic layer was dried over $Na_2SO_4$, filtered, and concentrated. The residue was purified by chromatography on neutral alumina using 78/20/2/0.5 $CHCl_3$/MeOH/$H_2O$/15% $NH_4OH$ as the eluent. The appropriate fractions were pooled and concentrated. The residue was taken up in $CHCl_3$, washed with 1 M NaBr, dried ($Na_2SO_4$), and concentrated to afford the pure product.

Example III

Synthesis of (±)-N-(3'-N'-propyl-N',N',N'-trimethylammonium)-N,N-dimethyl-2,3-bis(lauryloxy)-1-propanaminium dibromide (Trimethyl-GAP-DLRIE, formula I)

DLP-DMA (0.25 g, prepared analogously to DMOP-DMA above) and 3-bromopropyl-trimethylammonium bromide (430 mg) were combined in DMF (5 mL) and stirred overnight at 75° C. under argon atmosphere to effect quaternization of the tertiary amine. The solvent was removed by distillation in vacuo, and the dry residue was purified by silica gel chromatography using 70/30 $CHCl_3$/MeOH as the eluent. The appropriate fractions were pooled and concentrated to afford the pure product.

Example IV

Synthesis of (±)-N,N-Bis(3'-N'-propyl-N',N',N'-trimethylammonium)-N-methyl-2,3-bis(tetradecyloxy)-1-propanaminium tribromide (Hexamethyl-BPA-DMRIE, formula I)

Bis(propylamino)-DMRIE (0.60 g) was treated with 9 M NaOH (0.7 mL) and $CH_3I$ (3 mL) in methanol (20 mL) at 0° C. to room temperature overnight to effect quaternization of both primary amines. The solvent was removed in vacuo, and the residue was purified by chromatography on neutral alumina using 78/20/2/0.5 $CHCl_3$/MeOH/$H_2O$/15% $NH_4OH$ as the eluent. The appropriate fractions were pooled and concentrated. The residue was taken up in $CHCl_3$, washed with 1 M NaBr, dried ($Na_2SO_4$), and concentrated to afford the pure product.

Example V

Synthesis of (±)-N-(3-dimethylaminopropyl)-N,N-dimethyl-2,3-bis(myristoleyloxy)-1-propanaminium bromide (Dimethyl-GAP-DMORIE, formula I)

DMOP-DMA (2.2 g, prepared as above) and 1,3-dibromopropane (1 mL) were combined in DMF (20 mL) and stirred overnight at 85° C. under argon atmosphere to effect quaternization of the tertiary amine. The solvent was removed by distillation in vacuo, and the dry residue was purified by silica gel chromatography using 85/15 $CHCl_3$/MeOH as the eluent. The appropriate fractions were pooled and concentrated to afford the pure 3-bromopropyl-DMORIE intermediate. This intermediate (0.7 g) was refluxed with dimethylamine (10 mL, 2.0 M in MeOH) in methanol (10 mL) overnight. The solvent was removed in vacuo and the crude product was chromatographed on silica gel using 78/20/2 $CHCl_3$/MeOH/$H_2O$ as the eluent. The appropriate fractions were pooled and concentrated to afford the pure product.

Example VI

Synthesis of N-(3-Aminopropyl)-N-methyl-4,4-bis(oleyloxy)-piperidinium bromide (PA-DOMe-Pipd, formula II)

A solution of N-methyl-4-piperidone (5.03 g), oleyl alcohol (26.3 g), and p-TsOH (9.32 g) in benzene was refluxed for one hour with stirring, and the water removed by a Dean-Stark trap. After cooling to room temperature, the solution was diluted with ether and washed sequentially with 1 M NaOH and brine. The organic layer was dried ($Na_2SO_4$) and concentrated to afford the crude intermediate as an oil. This material was purified by silica gel chromatography employing a step gradient of $CHCl_3$ and 90/10 $CHCl_3$/MeOH as the eluents, affording 16.3 g pure product (DOMe-pipd). DOMe-pipd (7.8 g) was then combined with N-(3-bromopropyl) phthalimide (4.0 g) in dimethylformamide (20 mL) at elevated temperature (85° C., overnight) to effect quaternization of the piperidine ring. Distillation of the dimethylformamide in vacuo followed by silica gel chromatography employing a step gradient of 95/5 $CHCl_3$/MeOH and 90/10 $CHCl_3$/MeOH as the eluents, afforded 6.0 g pure product (γ-Phth-DOMe-pipd). Deprotection of the primary amine was accomplished by treatment of the phthalimide with anhydrous hydrazine (4.1 mL) in anhydrous ethanol (100 mL) and propargyl alcohol (10 eq.). Filtration, evaporative removal of the solvent, basic extraction (0.1 M NaOH), alumina chromatography, and 1 M NaBr wash afforded the title compound.

The following example demonstrates the surprising finding that the cationic lipid compounds of formula I and/or II:co-lipid complexed with an antigen-encoding pDNA can enhance subsequent immune response compared to presently known nucleic acid immunization methods when administered into murine or rabbit tissues, Example VII Formulation and In Vivo Study of Trimethyl-GAP-DMORIE/DPyPE in the Murine Flu Challenge Model Trimethyl-GAP-DMORIE/DPyPE (1:1 molar ratio, 2.25 mg total lipid) dry lipid films were prepared and suspended in 0.9% saline (1 mL). 0.7 mL of this suspension was added slowly to 0.7 mL of a cocktail containing plasmids encoding for NP and M2 influenza viral surface proteins in 20 mM PBS (2 mg/mL total plasmid) to afford the final pDNA/lipid formulation at 1 mg/mL (10 mM PBS, pDNA/lipid ratio at 4:1). The formulation was then diluted further with PBS to a concentration of 0.05 ug/uL prior to injection. Each mouse received 100 uL of pDNA/lipid formulation (0.05 ug/uL), injected bilaterally into the rectus femoris muscle at 0 and 3 weeks. Mice were given a lethal challenge of flu virus at week 6, and survival was measured three weeks later. Mice treated with either trimethyl- or dimethyl-GAP-DMORIE/DPyPE/pDNA formulations all exhibited high survival rates (80-100% protection).

B. Delivery Methods of Formulated DNA

The following examples demonstrate the surprising finding that the mode of delivering formulated DNA impacts both the humoral as well as cellular immune responses. All scientific and technical terms have the meanings as understood by one with ordinary skill in the art. The specific examples which follow illustrate the methods in which the compositions of the present invention may be administered and are not to be construed as limiting the invention in sphere or scope.

Materials and Methods

Reagents

The nonionic tri-block copolymer (poloxamer) CRL1005 was obtained from CytRx Corporation (Los Angeles, Calif.). The cationic surfactant Benzalkonium chloride 50% solution NF (BAK, BTC 50® NF) was obtained from Stepan Company (Northfield, Ill.). Vaxfectin® was made in accordance with U.S. Pat. Nos. 6,586,405 and 7,105,574 which are incorporated herein by reference.

Plasmid Constructs

Influenza antigen plasmids VR4752 (H1 HA; negative control plasmid used in influenza challenge studies), VR4750 (H3 HA; positive control plasmid used in influenza challenge studies), VR4759 (encoding M2) and VR4762 (encoding NP) were constructed by inserting the influenza H1 HA, 113 HA, M2, or NP gene open reading frame sequence into expression plasmid VR10551 containing the human CMV immediate early 1 promoter/enhancer and intron A, modified rabbit β-globin terminator and kanamycin resistance gene as previously described (Jimenez, G. S., et al., Hum Vaccine, 3(5), 157-64 (2007). Plasmid VCL6365 encoding a secreted form of human CMV gB antigen lacking the transmembrane and cytoplasmic domains was constructed as previously described (Selinsky, C., et al., Hum Vaccine, 1(1), 16-23 (2005).

Preparation of Adjuvant and Immunogenic Compositions

Cytofectin:Co-lipid Adjuvant Formulations

Cytofectin:co-lipid adjuvant formulations were prepared as previously described (Hartikka, J., et al., Vaccine, 19(15-16), 1911-23 (2001); Jimenez, G. S., et al., Hum Vaccine, 3(5), 157-64 (2007). DMRIE:DOPE (DM:DP) consists of a 1:1 molar mixture of DMRIE and DOPE, and Vaxfectin® consists of a 1:1 molar mixture of VC1052 and DPyPE. Both DM:DP and Vaxfectin® were prepared as dried lipid films by mixing equimolar chloroform solutions of DM and DP or VC1052 and DPyPE, respectively. The chloroform was evaporated under a stream of nitrogen and then the vials were placed under vacuum overnight. For DM:DP, the lipid film was reconstituted with 1 ml of PBS, followed by vortexing for 5 minutes, while the Vaxfectin® lipid film was reconstituted with 1 ml of 0.9% saline, followed by vortexing for 5 minutes. The lipids were diluted further to the required concentration in the respective resuspension vehicles. DM:DP vaccine formulations were prepared at a final pDNA (phosphate):cationic lipid molar ratio of 4:1 by adding an equal volume of lipid (at twice the final concentration in PBS) to pDNA (at twice the final concentration in PBS). The lipid was added to pDNA rapidly as a bolus using a needle and syringe, and after the addition the vial was inverted several times to produce a uniform suspension. Vaxfectin® vaccine formulations were prepared at a final pDNA (phosphate):cationic lipid molar ratio of 4:1 by adding an equal volume of lipid (at twice the final concentration in 0.9% saline) to pDNA (at twice the final concentration in 0.9% saline, 20 mM sodium phosphate, pH 7.2). The lipid was added in a gentle stream down the side of the pDNA vial, followed by gentle inversion until the suspension was uniform. All vaccine formulations were prepared on the day of the injection.

Poloxamer 02A (CRL1005+BAK+pDNA) Formulation

Poloxamer 02A (CRL1005+BAK+pDNA) formulations were prepared as previously described (Selinsky, C., et al., Hum Vaccine, 1(1), 16-23 (2005) and Hartikka, J., et al. J. Gene Medicine, in press (2008)). Briefly, the required concentration of pDNA in PBS (0.9% sodium chloride+10 mM sodium phosphate, pH 7.2) was stirred on ice and the required amount of poloxamer CRL1005 was added using a positive displacement pipette. The solution was stirred on ice until the poloxamer dissolved and then the required concentration of BAK dissolved in PBS was added. The solution was then thermocycled through the cloud point (7-12° C.) several times to ensure homogeneity, filter sterilized through a Millipore Steriflip disposable vacuum filtration system (Millipore, Billerica, Mass.) at 4° C. and stored frozen. Prior to injection, the vaccine was thawed at ambient temperature (25° C.) and, if required, diluted to the required pDNA concentration with PBS above the cloud point of CRL1005.

Animal Immunizations

All animal procedures were approved by the Institutional Animal Care and Use Committee (IACUC) and complied with the standards set forth in the Guide for the Care and Use of Laboratory Animals (ILAR, 1996) and the Animal Welfare Act and Animal Care Regulations.

For intradermal (ID) immunization with needle & syringe, mice received either two ID injections (20 til/site) into the dorsal/flank skin, or one ID injection (20 til/site) into the skin over the gastrocnemius muscle, using a 3/10 cc insulin syringe with a 28G½" needle.

Epidermal/intradermal immunization of mice was performed using UltraEnhancer® device (PMT/Permark, Chanhassen, Minn.), which is an oscillating multi-needle intradermal (OMNI) delivery device. The device has been approved in Europe and in the USA for medical and cosmetic micropigmentation ("tattooing") applications in humans. Histochemical analysis has shown that cells in the upper layers of the dermis and the epidermis get transfected with the antigen-expressing plasmid when pDNA vaccine is delivered to the skin using such a device (Bins, A. D., et al., Nat Med, 11(8), 899-904 (2005).

OMNI device was used with a sterile 9-needle array (PMT/Permark) consisting of a 3×3 cluster of solid non-injecting steel needles. The handpiece of the device was modified by inserting a metal ring between the nose cone and the barrel. Due to this adjustment, penetration depth of the 9-needle array used for mice was limited to approximately 0.5 mm. The approximate diameter of the needle array was 1 mm in each direction.

The immunization procedure was similar to the one previously published (Bins, A. D., et al., Nat. Med., 11(8), 899-904 (2005). Briefly, mice were anesthetized using an appropriate agent such as Isoflurane, and an area approximately the size of 1 cm² was shaved in the skin over the gastrocnemius muscle of the left leg. The skin was wiped with alcohol and let to dry before vaccination. Twenty microliters of vaccine solution was applied topically on the skin (single unilateral application), immediately followed by treatment with OMNI device for 16 seconds with the needle array oscillating at the maximum speed 8,000 RPM (=133 Hz). Approximately 0.5 cm² (0.5 cm wide×1.0 cm long) large area on the skin was treated by moving the array up and down (1-2 up-and-down movements/second). Mice were allowed to recover from anesthesia without covering the treated area.

The same procedure was repeated on day 3 and 6 by choosing an adjacent skin area in the left leg. Vaccinations were done in following sequence: lateral (day 0), caudal (day 3), and medial (day 6) face of skin over the left gastrocnemius muscle. Boost immunizations were administered into the contralateral right leg skin on day 21, 24, and 27 in the same sequence: lateral, caudal, and medial face of skin over the right gastrocnemius muscle.

Immunization of Mice

Groups of 6- to 10-week old female BALB/c mice (Harlan-Sprague-Dawley, Indianapolis, Ind.) received bilateral intramuscular injections into the rectus femoris with pDNA formulation in 20-50 µl PBS/leg using a disposable ³⁄₁₀ cc insulin syringe with a 28G½" needle (Becton-Dickinson, Franklin Lakes, N.J.) as previously described (Hartikka, J., et al., *Vaccine*, 19(15-16), 1911-23 (2001); Leamy, V. L., et al., *Hum Vaccine*, 2(3), 113-8 (2006).

For intradermal (ID) immunization with needle & syringe, mice received two ID injections (20 µl/site) into the dorsal/flank skin (or the skin over the gastrocnemius muscle) using a ³⁄₁₀ cc insulin syringe with a 28G½" needle.

Transdermal immunization of mice was performed using UltraEnhancer® device (PMT/Permark, Chanhassen, Minn.), which is an oscillating multi-needle intradermal (OMNI) delivery device. The device has been approved in Europe and in the USA for medical and cosmetic micropigmentation ("tattooing") applications in humans. The device was used with a sterile 9-needle array (PMT/Permark) consisting of a 3×3 cluster of solid non-injecting steel needles. The approximate diameter of the needle array was 1 mm in each direction.

The immunization procedure was similar to the one previously published (Bins, A. D., et al., *Nat Med*, 11(8), 899-904 (2005). Briefly, mice were anesthetized using an appropriate agent, and an area approximately the size of 1 cm² was shaved in the skin over the gastrocnemius muscle of the left leg. The skin was wiped with alcohol and let to dry before vaccination. Vaccine solution was applied topically on the skin, immediately followed by treatment with OMNI device for 16 seconds with the needle array oscillating at the maximum speed 8,000 RPM (=133 Hz). The 9-needle array was adjusted so that the penetration depth was ~0.5 mm. Approximately 0.5 cm² large area in the skin was treated by moving the array up and down. Mice were allowed to recover from anesthesia without covering the treated area. The same procedure was repeated on day 3 and 6 by choosing an adjacent skin area in the left leg. Vaccinations were done in following sequence: lateral, caudal, and medial face of skin over the left gastrocnemius muscle. Boost immunizations were administered into the contralateral right leg skin on day 21, 24, and 27 in the same sequence: lateral, caudal, and medial face of skin over the right gastrocnemius muscle.

Mice were bled via the ophthalmic venous plexus at indicated time points, and sera were stored at −20° C. until assayed for antigen-specific antibodies by ELISA. Splenocytes were harvested at indicated time points and antigen-specific T-cell responses were measured by IFN-γ ELISPOT assay.

Immunization of Rabbits

Female New Zealand White rabbits (5-6 months of age, approximately 2-3 kg) were injected in the vastus lateralis muscle with pDNA±formulation in PBS using a 22 gauge 1 inch needle as previously described (Hartikka, J., et al., *Vaccine*, 19(15-16), 1911-23 (2001); Leamy, V. L., et al., *Hum Vaccine*, 2(3), 113-8 (2006).

The needle-free injection device Biojector®2000 (Bioject Incorporated, Portland, Oreg.) is a $CO_2$ powered jet injection system. The injection site was shaved, cleaned with alcohol and the intramuscular injections (vastus lateralis muscle, 500 µL per site) with Biojector®2000 using Biojector syringe #2 were performed as previously described (Hartikka, J., et al., *Vaccine*, 19(15-16), 1911-23 (2001). ID vaccinations with Biojector®2000 were performed in the skin area overlaying vastus lateralis muscle (100 µL per site) using Biojector syringe #2 fitted with an intradermal spacer. No anesthesia was used for these procedures.

Antibody ELISA Assays

Serum anti-NP IgG titers were measured in an indirect ELISA assay using ninety-six well plates (Corning Incorporated, Corning, N.Y.) coated with influenza A/PR/8/34 nucleoprotein (NP) purified from recombinant baculoviral extracts as previously described (Hartikka, J., et al., *Vaccine*, 19(15-16), 1911-23 (2001). Serum anti-M2 IgG titers were measured in an indirect ELISA assay using ninety-six well plates coated with influenza M2e peptide containing the first 23 amino acids of the M2 consensus sequence (MSLLTEVET-PRINEWGCRCNDSS (SEQ. ID. NO. 1); Biosynthesis Custom Peptide, Lewisville, Tex.) as previously described (Jimenez, G. S., et al., *Hum Vaccine*, 3(5), 157-64 (2007). CMV gB-specific IgG antibody responses were measured by ELISA using ninety-six well plates coated with recombinant gB protein (Austral Biologicals, San Ramon, Calif.) as previously described (Selinsky, C., et al., *Hum Vaccine*, 1(1), 16-23 (2005). Humoral responses in some serum samples were analyzed using commercially available Anti-hCMV ELISA kits (BioCheck, San Diego, Calif.). Endpoint titers were determined as the reciprocal of the last dilution at which the absorbance value of the test serum was at least twice that of the absorbance value of the background established with pre-immune serum.

IFN-γ ELISPOT Assays

Mice were sacrificed at indicated time points, splenocytes were harvested and antigen-specific T-cell responses were measured by IFN-γ ELISPOT assay as previously described (Selinsky, C., et al., *Hum Vaccine*, 1(1), 16-23 (2005). Briefly, ImmunoSpot plates (Millipore, Billerica, Mass.) were coated with rat anti-mouse IFN-γ monoclonal antibody (BD Pharmingen, San Diego, Calif.) and blocked with RPMI-1640 medium containing 10% (vol/vol) defined fetal bovine serum (FBS, Hyclone, Logan, Utah). Splenocyte suspensions were seeded in quadruplicate wells of ImmunoSpot plates at 1×10⁶ cells/well in RPMI-1640 medium containing 25 mM HEPES buffer and L-glutamine (Invitrogen, Carlsbad, Calif.) supplemented with 10% (v/v) FBS, 55 µM β-mercaptoethanol (Invitrogen, Carlsbad, Calif.), 100 U/mL of penicillin G sodium salt and 100 µg/mL of streptomycin sulfate (Invitrogen, Carlsbad, Calif.). For detection of NP-specific IFN-γ secreting CD8+ T-cells, splenocytes were stimulated with the NP class I peptide, TYQRTRALV (SEQ. ID. NO. 2), at 4 µg/ml with 1 unit/ml of recombinant mouse IL-2 (Roche, Indianapolis, Ind.). For detection of NP-specific IFN-γ secreting CD4+ T-cells, splenocytes were stimulated with a cocktail of three NP class II peptides, FWRGENGKTRSAYERMC-NILKGK (SEQ. ID. NO. 3), AVKGVGTMVME-LIRMIKRGINDRN (SEQ. ID. NO. 4), RLIQNSLTIERMV-LSAFDERRNK (SEQ. ID. NO. 5) at 10 µg/ml each. After overnight incubation at +37° C. in 5% $CO_2$, captured IFN-γ from stimulated cells was detected by the sequential addition of biotin-labeled rat anti-mouse IFN-γ monoclonal antibody (1:1000 dilution, BD Pharmingen, San Diego, Calif.) and horseradish peroxidase-labeled avidin D (Vector Labs, Burlingame, Calif.). Spots produced by the conversion of 3-amino-9-ethylcarbazole substrate (AEC, Vector Labs, Burlingame, Calif.) were quantified using a C.T.L. ImmunoSpot Analyzer (Cellular Technology Ltd., Cleveland, Ohio). For each test group, the average background count derived from unstimulated cells was subtracted from counts obtained from each well of stimulated cells. Data were presented as the number of antigen-specific IFN-γ producing T-cells, designated as spot forming units (SFU) per million splenocytes (SFU/10⁶ cells).

Influenza Challenge Model

Mice were challenged with 1:10,000 dilution (50 PFU) of mouse-adapted influenza A/HK/68 p#6 as previously described (Jimenez, G. S., et al., *Hum Vaccine,* 3(5), 157-64 (2007). For the challenge, mice were anesthetized with ketamine by i.p. injection and inoculated intra-nasally with 0.02 ml of virus. Mice were monitored for recovery after infection, and then monitored daily for symptoms of disease, loss in body mass and survival through day 21 post-challenge.

Statistical Evaluations

Statistical analysis was performed using either Kruskal-Wallis one-way ANOVA, Student's t-test, or the non-parametric Mann-Whitney rank sum test (SigmaStat version 2.03, Systat Software, Inc., Point Richmond, Calif.).

1. Intradermal Delivery

Example VIII

Cytofectin:Co-Lipid Vaccine Formulations Delivered Either IM or ID with Needle & Syringe Enhance Humoral Immune Responses in Mice The purpose of the present example (FIG. 1) is to demonstrate the adjuvant effect of Vaxfectin® and DMRIE:DOPE, which was included as another example of cytofectin:co-lipid adjuvant formulations, administered either IM or ID with needle & syringe in mice. Poloxamer-based formulation, which has been shown to increase the immunogenicity of pDNA vaccines (Selinsky, C., et al., *Hum Vaccine,* 1(1), 16-23 (2005) and Hartikka, J., et al. *J. Gene Medicine,* in press (2008)) was also included in the study.

Twelve female BALB/c mice per group were vaccinated with VR4762 pDNA encoding influenza NP antigen. Mice were vaccinated with the following formulations: 1) pDNA in PBS; 2) Vaxfectin® formulation; 3) DMRIE:DOPE (DM:DP) formulation; and 4) poloxamer 02A formulation. Mice received either bilateral intramuscular (IM) injections into rectus femoris muscle (20 µl/muscle), or two intradermal (ID) injections (20 µl/site) into the dorsal/flank skin with needle & syringe, Mice received 10 µg of VR4762 per immunization on Day 0 and 21. On day 35, sera were collected and anti-NP antibody responses were measured using an ELISA assay.

Vaxfectin® and DMRIE:DOPE formulations increased anti-NP titers approximately 4- and 2-fold, respectively, compared to unformulated pDNA in PBS, both, with IM and ID injections, and enhanced antibody responses more than poloxamer formulation. Furthermore, ID injections of cationic lipid formulations resulted in comparable or higher antibody titers than when the same vaccine formulation was injected IM.

Example IX

Figures 2, 2A:
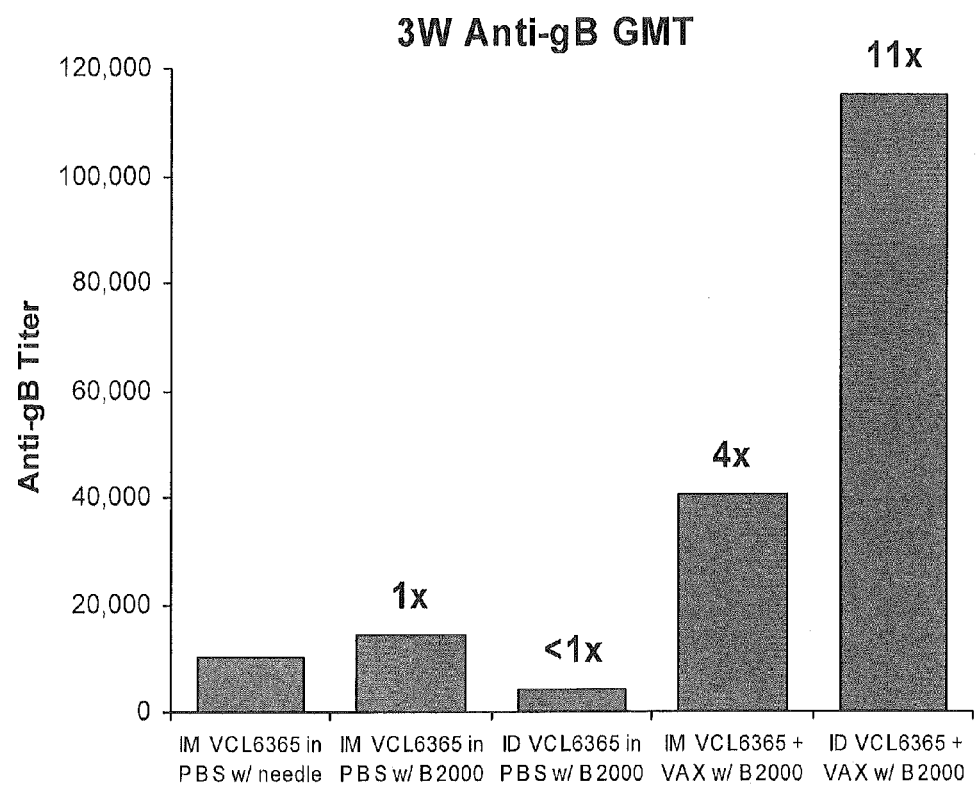

Vaxfectin®-Formulated pDNA Vaccine Delivered Either IM or ID Results in Stronger Humoral Immune Responses than Unformulated Vaccine in Rabbits The purpose of the present example (FIG. 2) is to compare IM vs. ID vaccine delivery routes administered either with needle & syringe or with Biojector®2000 device, and to demonstrate the adjuvant effect of Vaxfectin® formulations. Furthermore, the present example demonstrates that Vaxfectin® formulations are compatible with a needle-free delivery device.

New Zealand White Rabbits (n=6 per group) received either 0.1 mg of VCL6365 pDNA in PBS or 0.1 mg of Vaxfectin®-formulated VCL6365. Injections were performed either with needle & syringe or with B2000 device. On Day 0, rabbits received either a single IM vaccination in the right vastus lateralis muscle (500 µL per muscle), or a single ID vaccination in the skin area overlaying right vastus lateralis (100 µL per site). Identical boost vaccinations were administered on Day 21. Rabbits were bled from the ear vein once a week.

Three- and six-week serum samples were assayed for end-point anti-gB titers using recombinant gB protein to coat ELISA plates. More detailed time courses from select experimental groups were analyzed using commercially available Anti-hCMV ELISA kits.

Figure 2B:
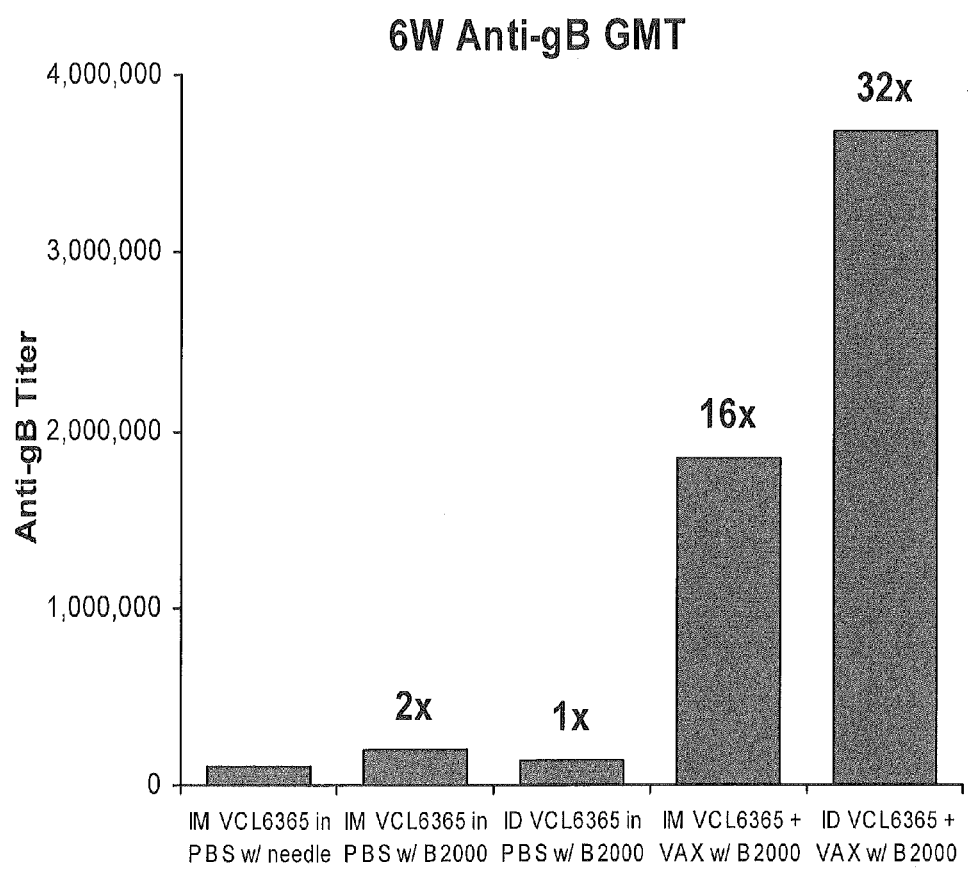
FIG. 2B shows anti-gB titers obtained three weeks after boost injections.
Figure 2C:
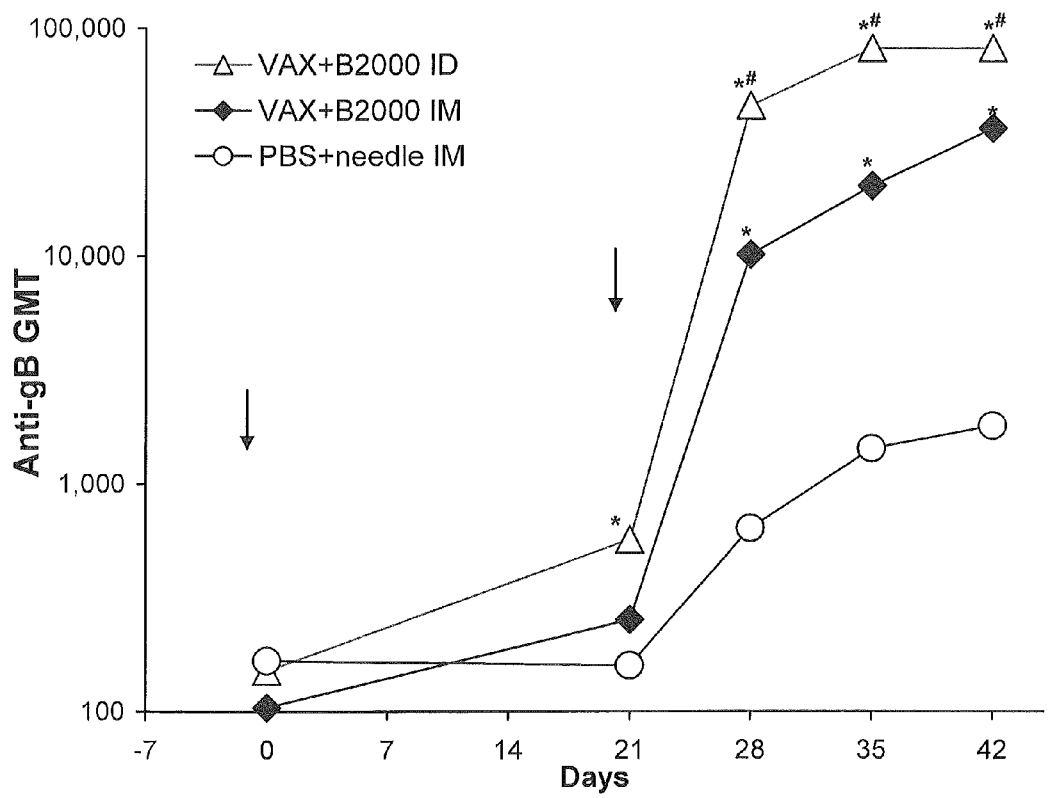
FIG. 2C shows more detailed time courses of humoral responses in rabbits immunized with unformulated pDNA injected IM with needle vs. responses obtained in rabbits immunized with Vaxfectin®-formulated pDNA delivered with Biojector® 2000 device.

Vaxfectin®-formulated vaccine resulted in markedly stronger humoral immune responses than obtained with unformulated vaccine, both, three weeks after a single injection (FIG. 2A) and three weeks after boost injection (FIG. 2B). Furthermore, Vaxfectin® formulation delivered ID with B2000 device resulted in significantly higher antibody titers than when the same vaccine dose and formulation was delivered IM with B2000, and significantly better responses than when unformulated pDNA vaccine was injected IM with needle & syringe (FIG. 2C).

Example X

Cytofectin:Co-Lipid Formulations Result in Stronger Humoral Immune Responses than Obtained with Poloxamer-Based pDNA Vaccine Formulations, and Demonstrate a Dose-Sparing Effect in Rabbits The purpose of the present example (FIG. 3) is to compare humoral immune responses obtained in rabbits with cytofectin:co-lipid formulations to responses obtained with poloxamer-based 02A formulation (poloxamer CRL1005+BAK+pDNA), which previously has been shown to increase the immunogenicity of pDNA vaccines compared to unformulated pDNA injected in PBS (Selinsky, C., et al., *Hum Vaccine,* 1(1), 16-23 (2005) and Hartikka, J., et al. *J. Gene Medicine,* in press (2008)).

New Zealand White Rabbits (n=6 per group) were vaccinated either with poloxamer 02A (CRL1005+BAK+VCL6365 pDNA) formulations (0.1 mg delivered either ID or IM with B2000, or 2.5 mg delivered IM with B2000), or with cytofectin:co-lipid formulations (0.1 mg of VCL6365 formulated with DMRIE:DOPE [D:D] and delivered ID with B2000, or 0.1 mg of VCL6365 formulated with Vaxfectin® and injected IM with needle & syringe). On Day 0, rabbits received either a single IM vaccination in the right vastus lateralis muscle (500 µL per muscle), or a single ID vaccination in the skin area overlaying right vastus lateralis (100 µL per site). Identical boost vaccinations were administered on Day 21. Rabbits were bled from the ear vein once a week.

Six-week serum samples were assayed for end-point anti-gB titers using recombinant gB protein to coat ELISA plates. More detailed time courses from select experimental groups were analyzed using commercially available Anti-hCMV ELISA kits.

Figures 3, 3A:
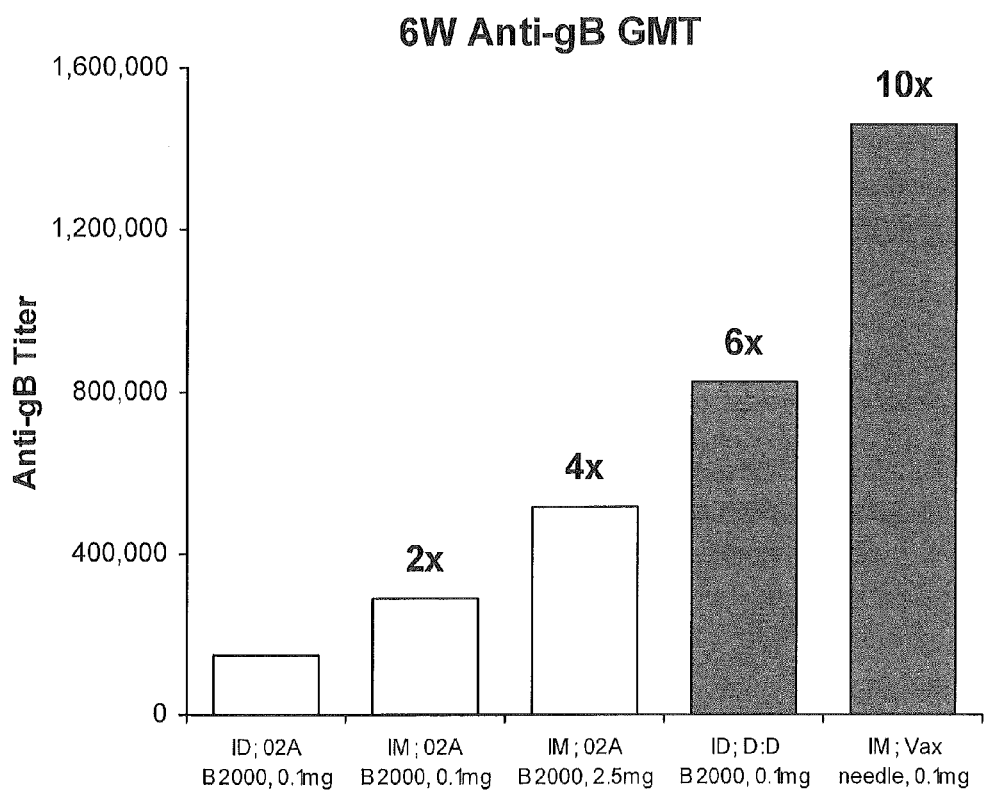
FIG. 3 consists of two bar graphs (3A and 3B) comparing humoral immune responses obtained in rabbits with pDNA vaccine formulated with poloxamer CRL1005+BAK to responses obtained with cytofectin:co-lipid vaccine formulations delivered either IM with needle & syringe, or ID with Biojector® 2000 device.
FIG. 3A shows anti-gB geometric mean titers (GMT) obtained three weeks after boost injections.
Figure 3B:
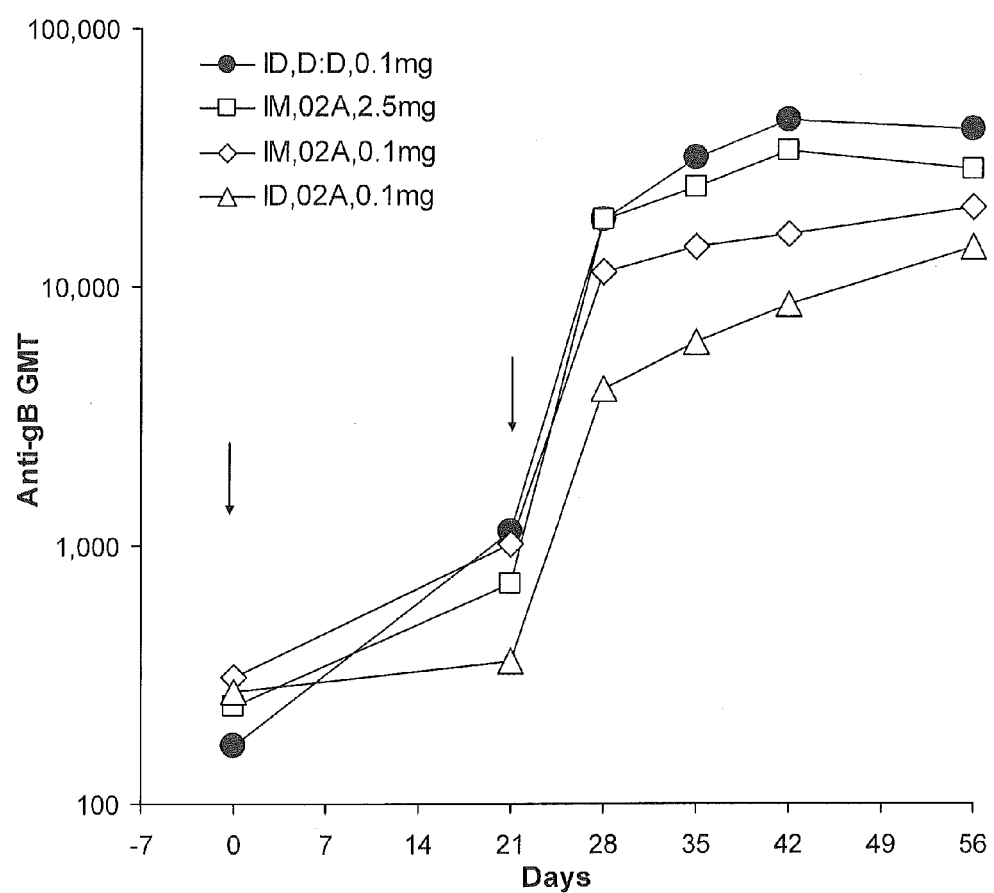
FIG. 3B shows more detailed time courses of humoral responses in rabbits immunized with poloxamer formulations vs. responses obtained in rabbits immunized with DMRIE:DOPE-formulated pDNA delivered ID with Biojector® 2000 device (B2000).

When the same dose of pDNA vaccine was delivered ID, DMRIE:DOPE formulation, a representative cytofectimco-lipid formulation, was superior to 02A poloxamer formulation (FIG. 3A, 3B).

Cytofectin:co-lipid formulations resulted in significantly higher humoral responses than obtained with the same 0.1 mg dose of 02A poloxamer formulation injected either ID or IM, and comparable or higher responses than obtained when a 25-fold higher dose of 02A formulation was delivered IM with B2000 device, demonstrating a substantial dose-sparing effect obtained with cytofectin:co-lipid formulations injected either with needle & syringe, or delivered with B2000 device (FIG. 3A, 3B).

Example XI

ID Delivery of Vaxfectin® Formulations in Rabbits Result in Stronger Antibody Responses than IM Route, and Enable Dose Sparing The purpose of the present example (FIG. 4) is to compare IM vs. ID immunization routes in rabbits using Vaxfectin®-formulated pDNA and either Biojector®2000 device or needle & syringe.

New Zealand White Rabbits (n=6 per group) were immunized with various doses of VCL6365 pDNA formulated with Vaxfectin®. The vaccine was delivered either IM or ID with Biojector®2000 device. One group of rabbits was vaccinated with 0.1 mg dose of Vaxfectin®-formulated VCL6365 injected IM with needle & syringe. On Day 0, rabbits received either a single IM vaccination in the right vastus lateralis muscle (500 µL per muscle), or a single ID vaccination in the skin area overlaying right vastus lateralis (100 µL per site). Identical boost vaccinations were administered on Day 21. Rabbits were bled from the ear vein once a week.

Six-week serum samples were assayed for end-point anti-gB titers using recombinant gB protein to coat ELISA plates. More detailed time courses from select experimental groups were analyzed using commercially available Anti-hCMV ELISA kits.

Figures 4, 4A:
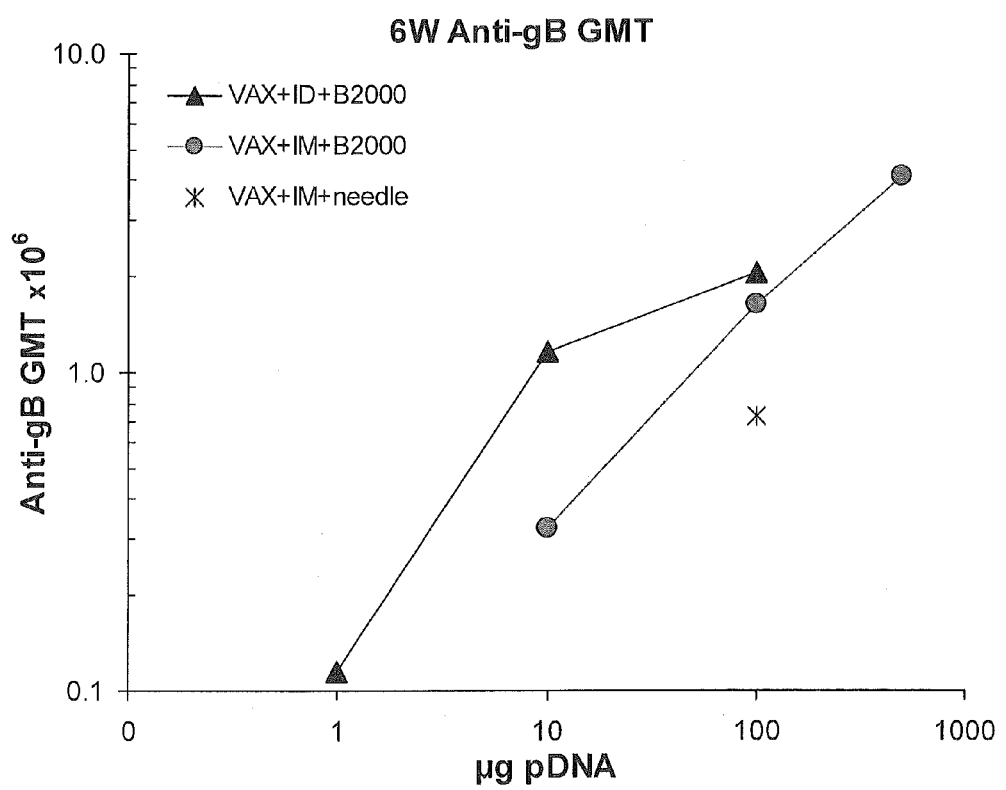
FIG. 4 consists of three graphs (4A, 4B and 4C) comparing IM vs. ID delivery routes in rabbits using Vaxfectin®-formulated pDNA and Biojector® 2000 device vs. IM injections performed with needle & syringe.
FIGS. 4A & 4B show 6-week anti-gB geometric mean titers (GMT) obtained in rabbits vaccinated with various doses of VCL6365 pDNA formulated with Vaxfectin®, and immunized either via IM or ID route.
Figure 4B:
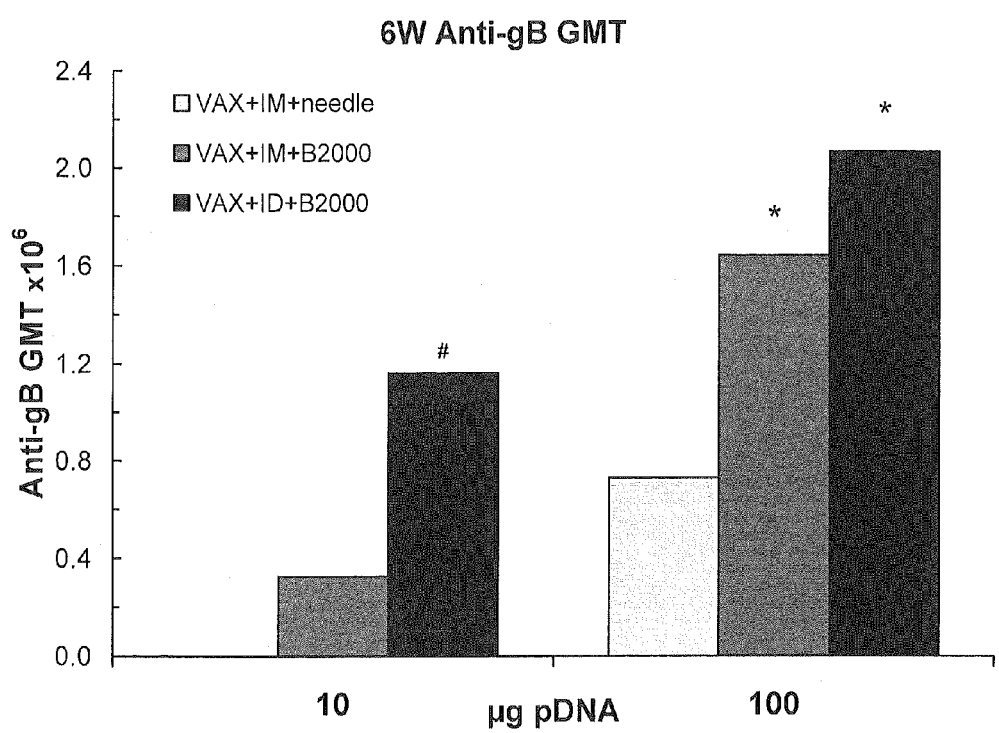

ID delivery of Vaxfectin® formulated pDNA vaccine resulted in stronger humoral immune responses than when the same formulations were delivered IM (FIGS. 4A & 4B).

Figure 4C:
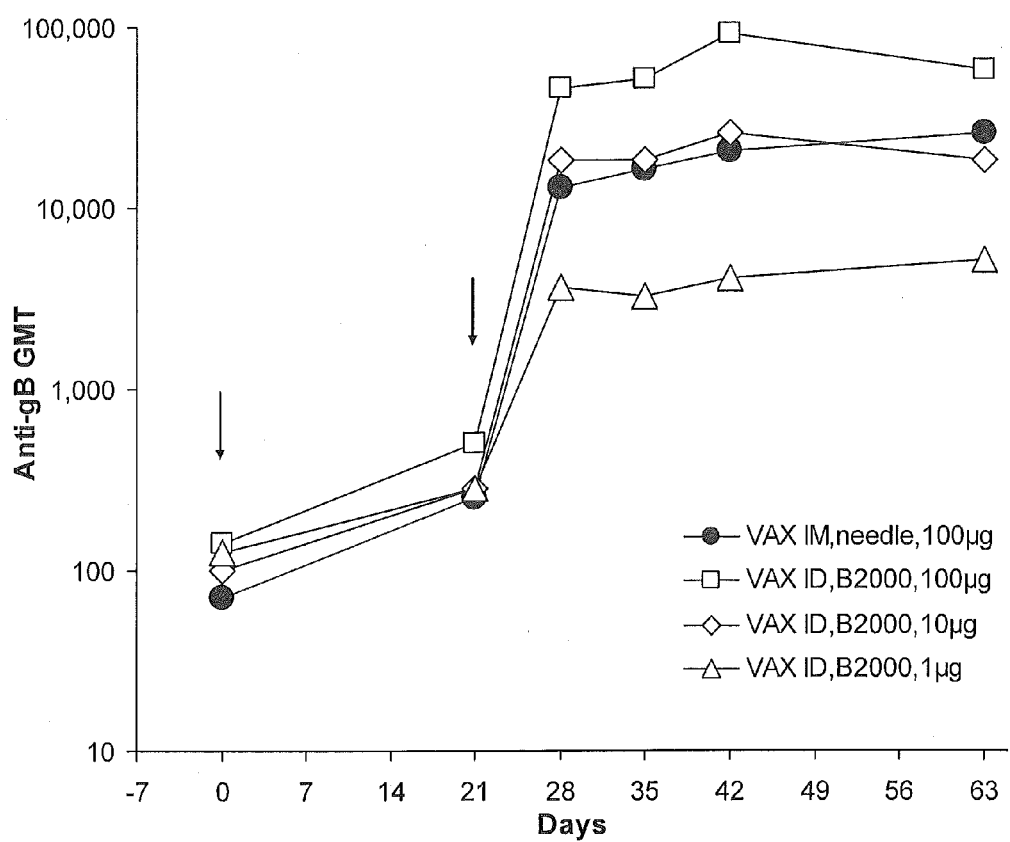
FIG. 4C shows more detailed time courses of humoral responses in rabbits immunized with Vaxfectin® formulations delivered ID with B2000 device vs. responses obtained with Vaxfectin® formulation injected IM with needle & syringe.

ID delivery of 10 µg of Vaxfectin® formulated pDNA resulted in antibody titers which were comparable to titers obtained by injecting 100 µg of Vaxfectin® formulated pDNA IM, demonstrating that ID vaccination route of Vaxfectin® formulations resulted in a 10-fold dose sparing effect (FIG. 4C).

2. Epidermal/Intradermal (Tattooing) Delivery of Formulated pDNA

Example XII

Epidermal/Intradermal Delivery of Vaxfectin®-Formulated pDNA Vaccine Results in Better Immune Responses than Obtained with ID Injections Using Needle & Syringe in Mice The purpose of the present example (FIG. 5) is to compare intradermal injections with needle & syringe to epidermal/intradermal pDNA vaccine delivery using OMNI device.

Mice (n=4 per group) were vaccinated with an equal mass of influenza antigen plasmids VR4759 (M2) and VR4762 (NP). Group A received a total of 100 µg of unformulated M2/NP pDNA applied topically on the skin (20 one site), followed by treatment with OMNI device. Group B received a total of 20 µg of M2/NP pDNA formulated with Vaxfectin® applied topically on the skin (20 µl, one site), followed by treatment with OMNI device. Group C received a total of 20 µg of M2/NP pDNA formulated with Vaxfectin® injected intradermally (20 µl, single injection) with needle & syringe. Vaccinations for all groups were done on Day 0, 3, 6, 21, 24, and 27.

On day 35, sera were collected and anti-M2 and anti-NP antibody responses were measured using an ELISA assay. On day 48, mice were challenged with 50 PFU of mouse-adapted influenza A/HK/68 virus, and monitored thereafter daily for survival and loss in body mass through day 21 post-challenge.

Figures 5, 5A:
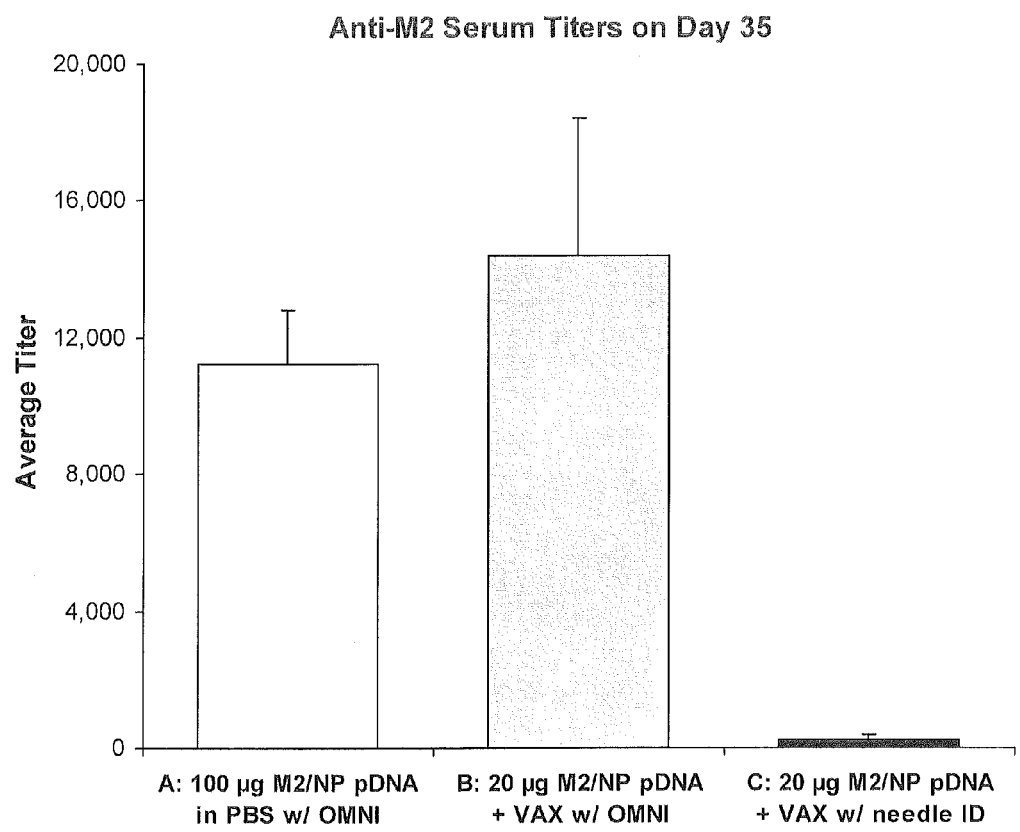
FIG. 5 consists of four graphs (5A, 5B, 5C and 5D) illustrating humoral immune responses and survival in influenza challenge model in mice immunized either with intradermal injections with needle & syringe, or by delivering the vaccine epidermally/intradermally with OMNI device.
FIG. 5A and FIG. 5B show average anti-M2 and anti-NP serum titers obtained in mice on Day 35, respectively.
Figure 5B:
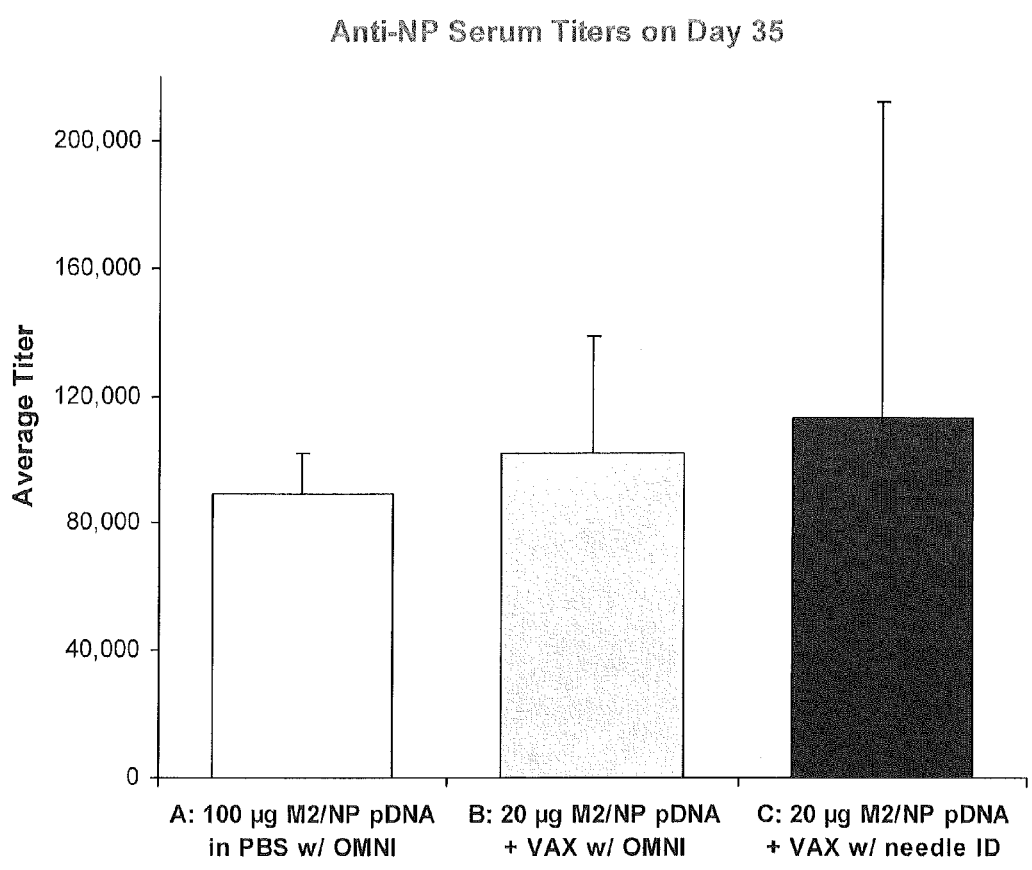

Humoral immune responses were comparable in group A and B, demonstrating a dose-sparing effect with Vaxfectin® (FIGS. 5A & 5B).

Anti-M2 humoral responses were superior in group B, which received Vaxfectin®-formulated vaccine epidermally/intradermally with OMNI device, compared to group C, which received the same dose of vaccine injected ID with needle & syringe (FIG. 5A).

Figure 5C:
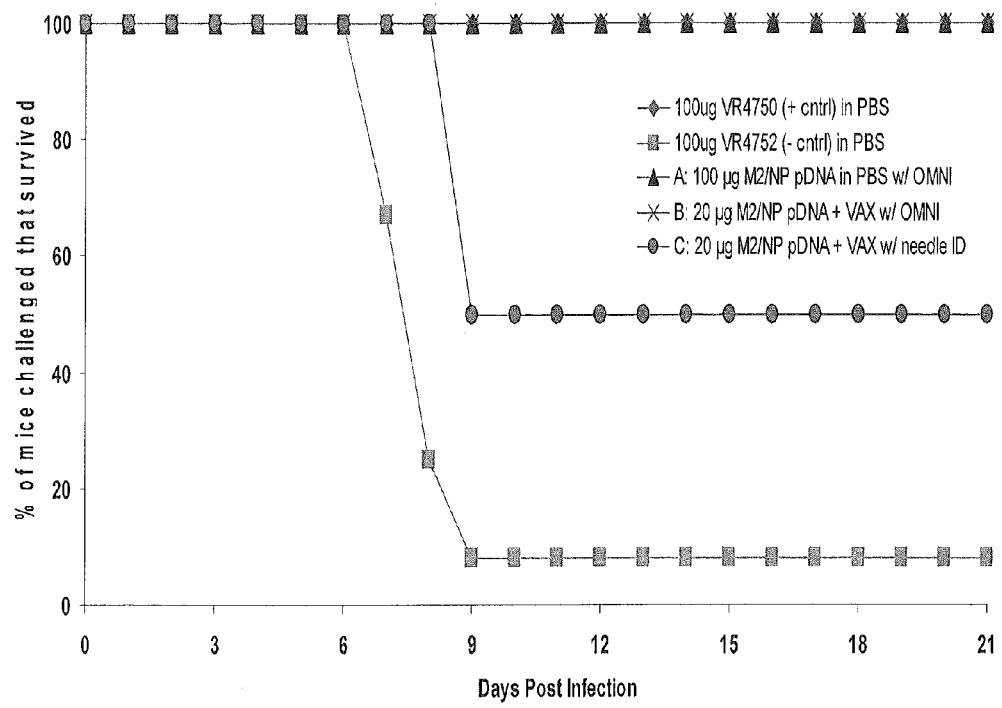
FIG. 5C and FIG. 5O show survival and average body mass of vaccinated mice challenged with influenza virus on Day 48, respectively.

Survival in influenza challenge model was better in group B, which received Vaxfectin®-formulated vaccine epidermally/intradermally with OMNI device, compared to group C, which received the same dose of vaccine injected ID with needle & syringe (FIG. 5C).

Figure 5D:
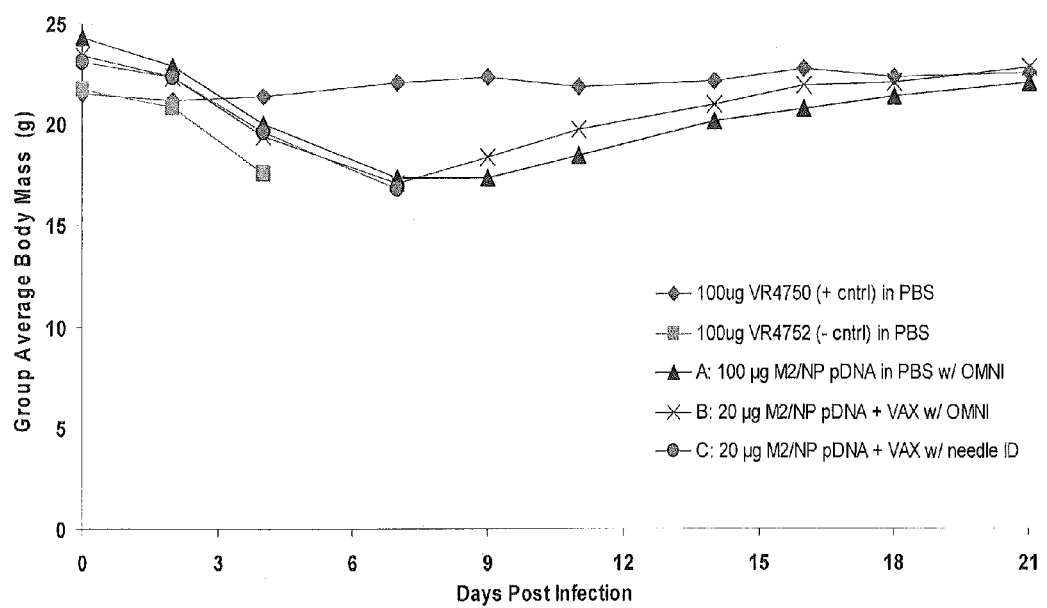

Recovery from weight loss was comparable or faster in group B compared to group A, demonstrating a dose-sparing effect with Vaxfectin® (FIG. 5D).

Example XIII

Epidermal/Intradermal Delivery of Vaxfectin®-Formulated pDNA Vaccine Results in Stronger Humoral as Well as Cellular Immune Responses, and Better Survival in a Challenge Model, than Obtained with IM or ID Injections Using Needle & Syringe in Mice The purpose of the present example (FIG. 6) is to compare intramuscular or intradermal injections using needle & syringe to epidermal/intradermal delivery with OMNI device by administering the same dose of Vaxfectin®-formulated pDNA vaccine.

In group A (n=15), mice were vaccinated with unilateral IM injections (20 µl, right rectus femoris muscle) using needle & syringe. In group B (n=15), mice were vaccinated with unilateral ID injections (20 skin area over the right gastrocnemius muscle) using needle & syringe. In group C (n=15), mice were vaccinated by applying the vaccine topically (20 µl, one site on the skin over the right gastrocnemius muscle), followed by treatment with OMNI device. All mice were immunized with the same 20 µg-dose of Vaxfectin®-formulated vaccine (equal mass of NP- and M2-encoding plasmids) administered on Day 0, 3, and 6.

On day 14, one set of mice were challenged with 50 PFU of mouse-adapted influenza A/HK/68 virus, and monitored thereafter daily for survival through day 21 post-challenge (n=10 mice per group). Another set of mice were kept until Day 21, when spleens were harvested to quantitate the number of NP-specific IFN-γ-secreting T-cells using an ELISPOT assay, and sera were collected for anti-NP and anti-M2 ELISA assays (n=5 mice per group).

Figures 6, 6A:
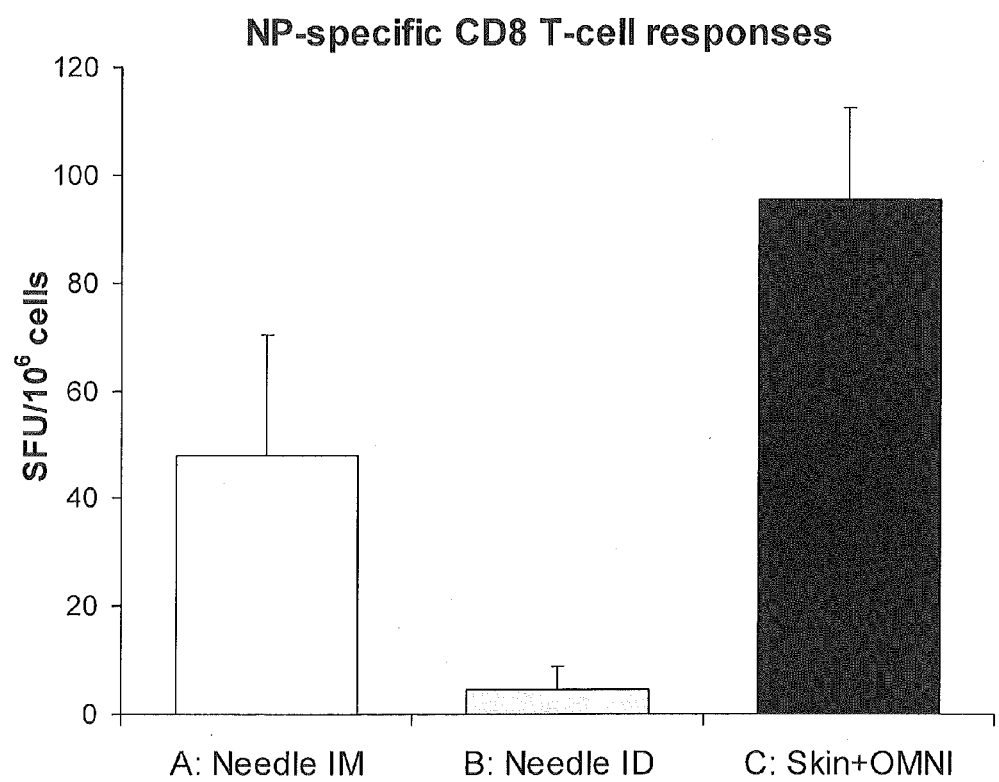
FIG. 6 consists of five graphs (6A, 6B, 6C, 6D and 6E) illustrating immune responses in mice vaccinated with the same dose of Vaxfectin®-formulated pDNA injected either IM or ID with needle & syringe, or delivered epidermally/intradermally with OMNI device, and demonstrates the survival of immunized mice in influenza challenge model.
FIG. 6A and FIG. 6B show NP-specific CD8+ and CD4+ T-cell responses on Day 21, respectively.
Figure 6B:
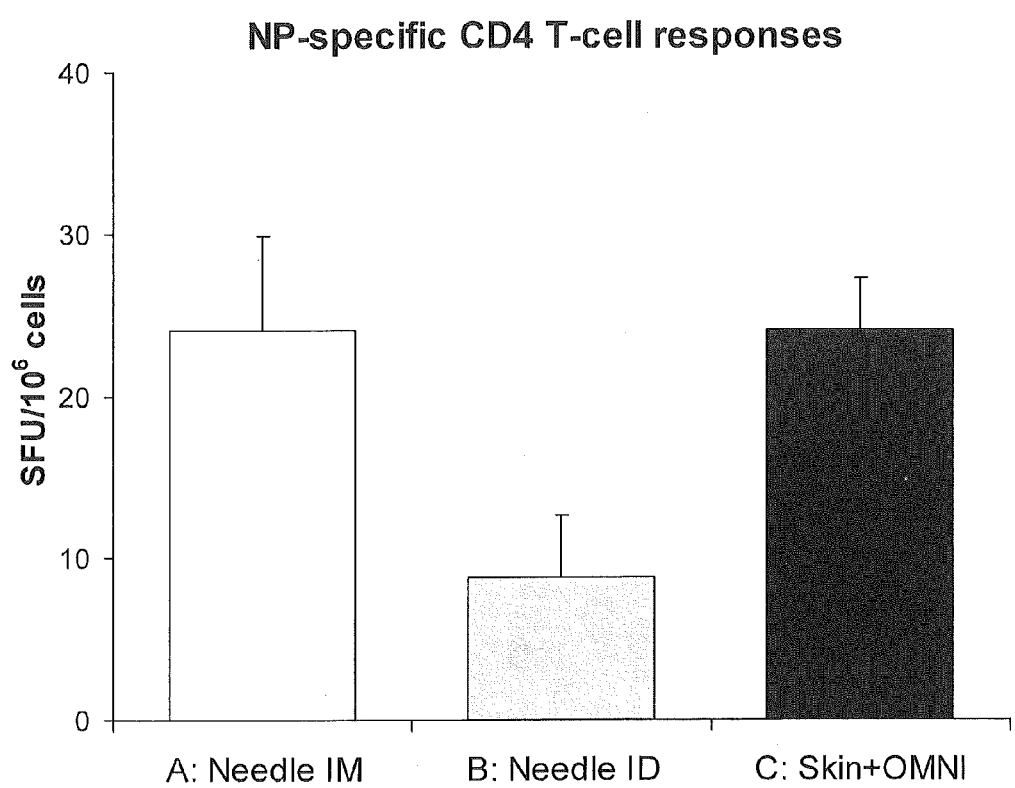

T-cell responses were comparable or stronger when Vaxfectin®-formulated vaccine was delivered epidermally/intradermally with OMNI device (C) than when injected IM (A) or ID (B) with needle & syringe (FIGS. 6A & 6B).

Figure 6C:
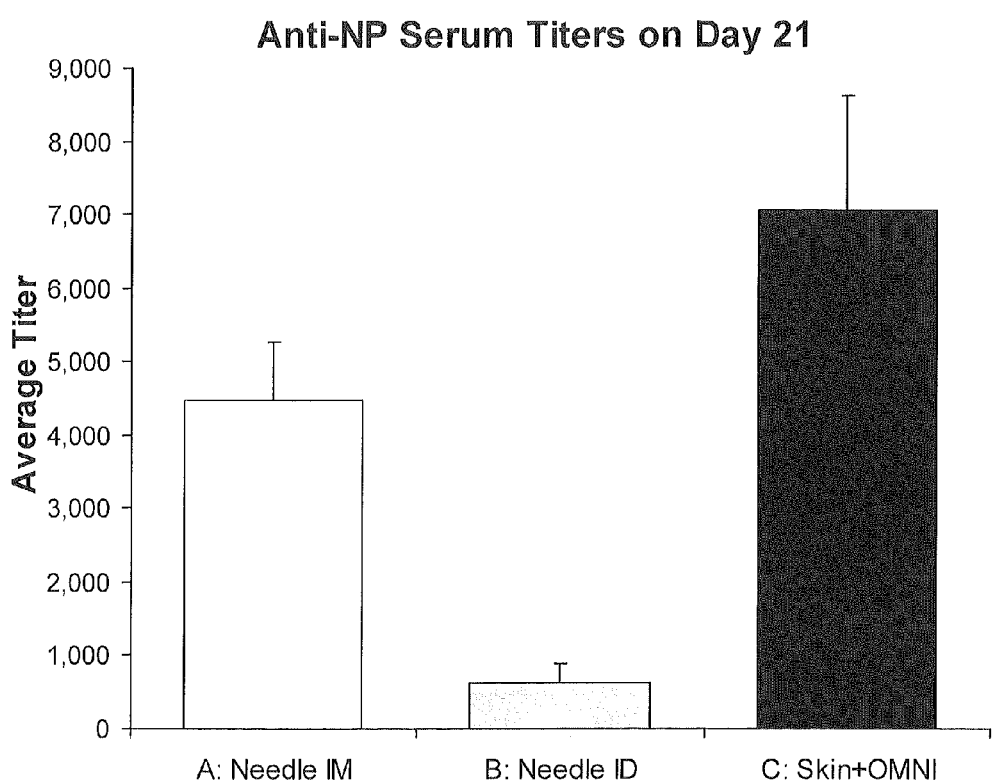
FIG. 6C and FIG. 6D show average anti-NP and anti-M2 serum titers on Day 21, respectively.
Figure 6D:
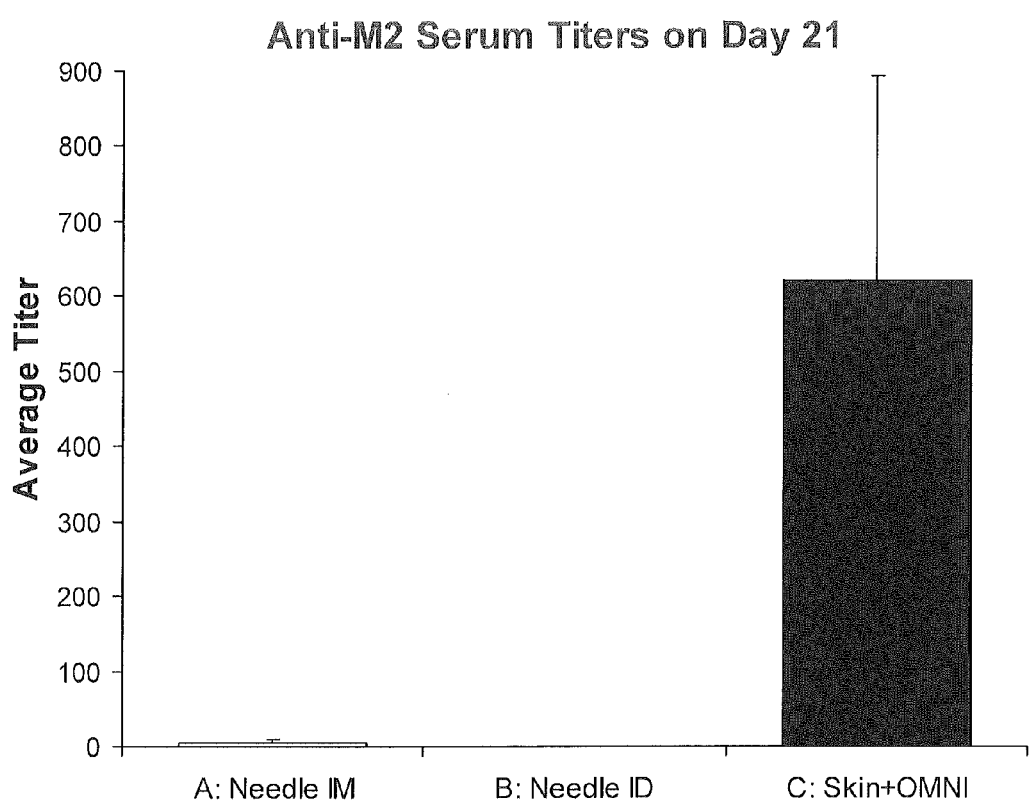

Anti-NP humoral responses were better, and anti-M2 responses were superior when Vaxfectin®-formulated vaccine was delivered epidermally/intradermally with OMNI device (C) than when injected IM (A) or ID (B) with needle & syringe (FIGS. 6C & 6D).

Figure 6E:
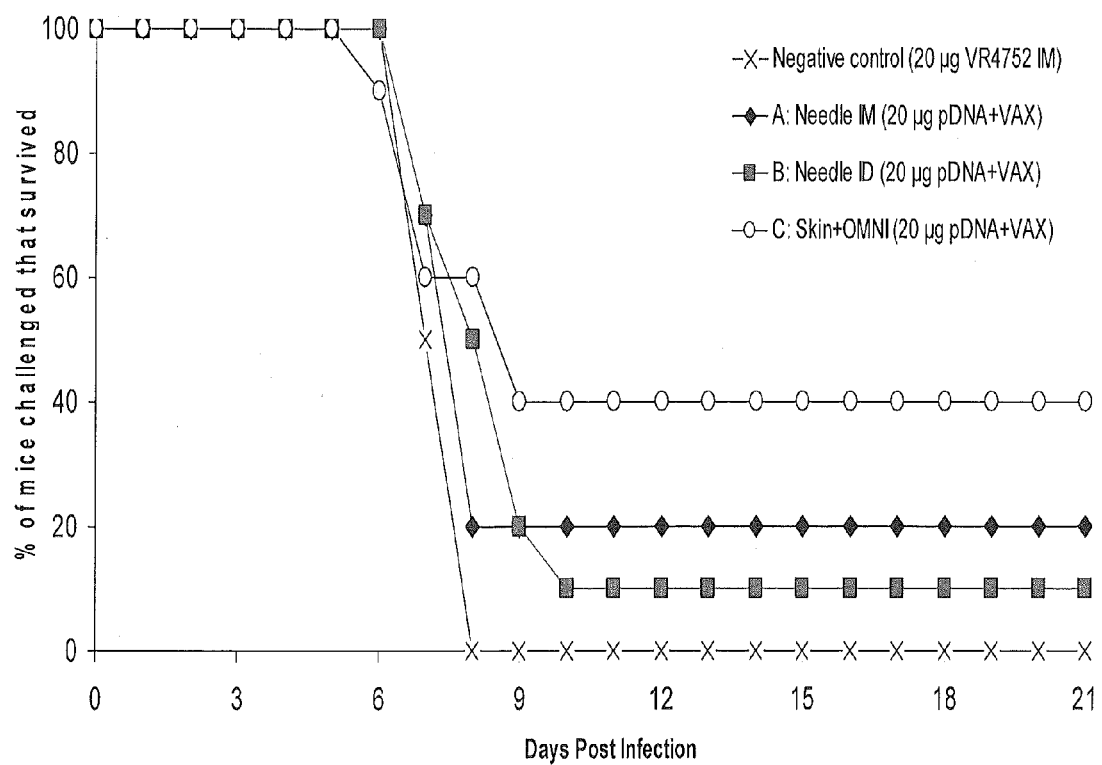
FIG. 6E illustrates survival of vaccinated mice challenged with influenza virus on Day 14.

Survival in influenza challenge model was better when Vaxfectin®-formulated vaccine was delivered epidermally/intradermally with OMNI device (40% protective immunity generated within 2 weeks in group C) than when the vaccine was injected IM (A) or ID (B) with needle & syringe (FIG. 6E).

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

OTHER REFERENCES

Bins, A. D., A. Jorritsma, et al. (2005). "A rapid and potent DNA vaccination strategy defined by in vivo monitoring of antigen expression." *Nat Med* 11(8): 899-904.

Hartikka, J., V. Bozoukova, et al. (2001). "Vaxfectin enhances the humoral immune response to plasmid DNA-encoded antigens." *Vaccine* 19(15-16): 1911-23.

Hartikka, J., A. Geall, et al. (2008). "Physical Characterization and in vivo Evaluation of Poloxamer-based DNA Vaccine Formulations." *J Gene Medicine: in press.*

Jimenez, G. S., R. Planchon, et al. (2007). "Vaxfectin-formulated influenza DNA vaccines encoding NP and M2 viral proteins protect mice against lethal viral challenge." *Hum Vaccine* 3(5): 157-64.

Leamy, V. L., T. Martin, et al, (2006). "Comparison of rabbit and mouse models for persistence analysis of plasmid-based vaccines." *Hum Vaccine* 2(3): 113-8.

Selinsky, C., C. Luke, et al. (2005). "A DNA-based vaccine for the prevention of human cytomegalovirus-associated diseases." *Hum Vaccine* 1(1): 16-23.

What is claimed is:

1. A method for immunizing a vertebrate comprising administering to the vertebrate an immunogenic composition in an amount sufficient to generate an immune response comprising one or more immunogens, and an adjuvant composition comprising a mixture of one or more compounds, wherein the compound is:

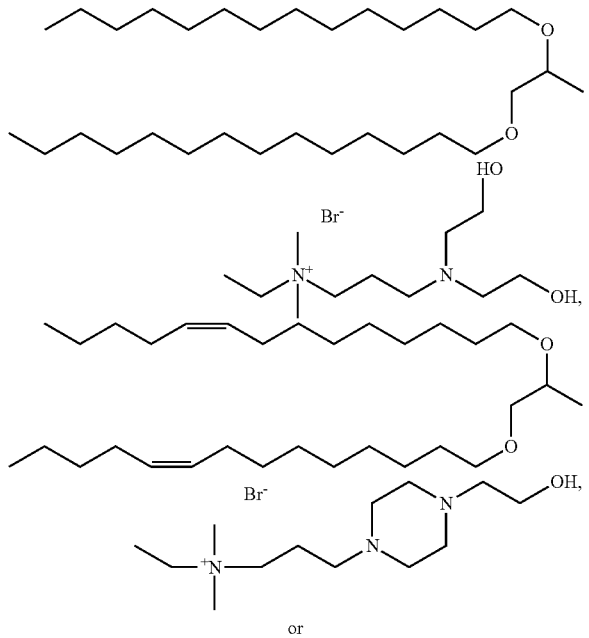

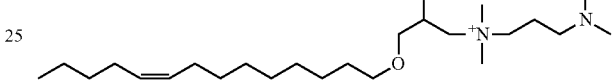

and one or more co-lipids.

2. The method of claim 1, wherein the co-lipid is a neutral lipid.

3. The method of claim 2, wherein the neutral lipid is a phosphatidylethanolamine, and/or a phosphatidylcholine, and/or a mono-, di-, or trialkylglycerol, and/or a mono-, di-, or triacylglycerol.

4. The method of claim 3, wherein the phosphatidylethanolamine is 1,2-dioleoyl-sn-glycero-3-phosphoethanolamine (DOPE) and/or 1,2-diphytanoyl-sn-glycero-3-phosphoethanolamine (DPyPE), and/or 1,2-dimyristoyl-glycero-3-phosphoethanolamine (DMPE).

5. The method of claim 4, wherein the phosphatidylethanolamine is 1,2-diphytanoyl-sn-glycero-3-phosphoethanolamine (DPyPE).

6. The method of claim 1, wherein the compound and the co-lipid are in molar ratio of from about 9:1 to about 1:9.

7. The method of claim 1, wherein the compound and the co-lipid are in molar ratio of from about 2:1 to about 1:2.

8. The method of claim 5, wherein the compound and DPyPE are in molar ratio of about 1:1.

9. The method of claim 1, wherein the immunogen is one or more immunogen-encoding polynucleotides, peptides or polypeptides, or polysaccharides.

10. The method of claim 1, wherein the administration is intradermal.

11. The method of claim 1, wherein the administration is into a tissue or cavity of the vertebrate.

* * * * *